(12) United States Patent
Wuori

(10) Patent No.: US 6,898,451 B2
(45) Date of Patent: May 24, 2005

(54) NON-INVASIVE BLOOD ANALYTE MEASURING SYSTEM AND METHOD UTILIZING OPTICAL ABSORPTION

(75) Inventor: Edward R. Wuori, Mounds View, MN (US)

(73) Assignee: Minformed, L.L.C., Mounds View, MN (US)

( * ) Notice: Subject to any disclaimer, the term of this patent is extended or adjusted under 35 U.S.C. 154(b) by 0 days.

(21) Appl. No.: 10/104,782

(22) Filed: Mar. 21, 2002

(65) Prior Publication Data

US 2003/0050541 A1 Mar. 13, 2003

Related U.S. Application Data

(60) Provisional application No. 60/277,758, filed on Mar. 21, 2001.

(51) Int. Cl.$^7$ .................................................. A61B 5/00
(52) U.S. Cl. ...................................... 600/322; 600/310
(58) Field of Search ............................... 600/309–310, 600/322–326, 316, 476, 473

(56) References Cited

U.S. PATENT DOCUMENTS

| | | | | |
|---|---|---|---|---|
| 3,596,057 | A | * 7/1971 | Arntz | 219/354 |
| 3,983,751 | A | * 10/1976 | Cipriano | 73/295 |
| 4,271,358 | A | * 6/1981 | Schwarz | 250/338.1 |
| 4,651,001 | A | 3/1987 | Harada et al. | |
| 5,069,214 | A | * 12/1991 | Samaras et al. | 600/323 |
| 5,197,470 | A | * 3/1993 | Helfer et al. | 600/342 |
| 5,348,003 | A | * 9/1994 | Caro | 600/310 |
| 5,355,880 | A | * 10/1994 | Thomas et al. | 600/326 |
| 5,361,758 | A | 11/1994 | Hall et al. | |
| 5,660,181 | A | * 8/1997 | Ho et al. | 600/408 |
| 5,755,226 | A | * 5/1998 | Carim et al. | 600/323 |
| 5,784,507 | A | * 7/1998 | Holm-Kennedy et al. | 385/31 |
| 5,817,007 | A | 10/1998 | Fodgaard et al. | |
| 5,900,632 | A | 5/1999 | Sterling et al. | |
| 6,039,697 | A | * 3/2000 | Wilke et al. | 600/310 |
| 6,119,031 | A | * 9/2000 | Crowley | 600/310 |
| 6,175,750 | B1 | * 1/2001 | Cook et al. | 600/310 |
| 6,198,949 | B1 | * 3/2001 | Braig et al. | 600/310 |
| 6,215,403 | B1 | * 4/2001 | Chan et al. | 600/323 |
| 6,341,257 | B1 | * 1/2002 | Haaland | 702/27 |
| 6,361,501 | B1 | * 3/2002 | Amano et al. | 600/500 |
| 6,452,179 | B1 | * 9/2002 | Coates et al. | 250/339.09 |
| 6,542,762 | B1 | * 4/2003 | Alam et al. | 600/310 |
| 2001/0034477 | A1 | * 10/2001 | Mansfield et al. | 600/316 |

FOREIGN PATENT DOCUMENTS

JP 62-250320 * 10/1987 ................ 374/121

OTHER PUBLICATIONS

Tatsyi Tigawa, Patient Monitoring, Wiley Encyclopedia of Electrical and Electronics Engineering Online, 1999.*

Webster's II New Riverside University Dictionary, Riverside Publishing Company,, 1994, p. 761.*

* cited by examiner

Primary Examiner—Max F. Hindenburg
Assistant Examiner—Matthew Kremer
(74) Attorney, Agent, or Firm—Fredrikson & Byron, P.A.

(57) ABSTRACT

A device and method for measuring the concentration of analytes in the blood of a portion of tissue. The device includes a sensor module, a monitor, and a processor (separate from or integral with the sensor module). The sensor module includes a radiation source for emitting radiation to the tissue; a collimator and narrow band filter for processing the radiation after it has transmitted through or been reflected by the tissue; and one or more sensors for sensing the transmitted or reflected radiation. The one or more sensors send a signal to the processor which algorithmically converts the radiation using linear regression or orthogonal functions to determine the concentration of one or more blood analytes. The device self-calibrates to eliminate error caused by variables such as skin character. The sensor module is integrated to reduce size and weight such that it is inobtrusive, and the monitor is compact for transport

31 Claims, 11 Drawing Sheets

NON-INVASIVE BLOOD ANALYTE MEASURING SYSTEM AND METHOD UTILIZING OPTICAL ABSORPTION

CROSS-REFERENCE TO RELATED APPLICATIONS

This application is entitled to the benefit of Provisional Patent Application Ser. No. 60/277,758 entitled "Noninvasive Infrared Blood Analyte Measuring System and Methods" by Edward Wuori, filed Mar. 21, 2001.

FIELD OF THE INVENTION

The present invention relates to a method and apparatus for non-invasive monitoring of various blood analytes in humans and other animals in the fields of medicine, sports medicine, military hardware, anemia treatment, diabetes treatment, and traumatic injury treatment.

BACKGROUND OF THE INVENTION

This invention relates to a non-invasive apparatus and methods for in vivo monitoring of the concentration levels of various blood analytes within a living subject, using optical absorption spectrophotometry. The device and methods may be used to simultaneously monitor several analytes found in the blood outside of a laboratory setting. The device and methods are able to resolve analytes down to approximately one mg/dL. Further, the device and methods are able to measure all blood analytes present at approximately one mg/dL, including glucose and lactate, for example.

Information concerning the concentrations of blood analytes is widely used to assess the health characteristics of people. For example, lactate is becoming the measurement of choice in sports and coaching to assess levels of conditioning for athletes and to prevent over-training. Lactate threshold and other related parameters are used to assess the aerobic and anaerobic status of athletes, are correlated to athletic performance, and may be used to "rank" athletes according to actual performance history. Lactate monitoring, as used in athletics, may also be useful for Military Academies, Army boot camps, and other physical training operations to assess the physical condition of trainees, to improve training programs, and to evaluate the effectiveness of training regimens on specific individuals. Lactate is also widely used to assess the medical condition of injured people. When serum lactate elevates after an injury, whether or not the lactate clears is correlated strongly with mortality, thus, measurement of serum lactate levels is a key tool in assessing treatment.

Likewise, the monitoring of blood glucose has long been an important tool in controlling diabetes in diabetic patients. Diabetes is a high maintenance disease, generally requiring several measurements of blood glucose daily. At present, this is typically accomplished using a glucometer, in which a fresh blood sample must be obtained for each measurement. Each measurement typically requires a new "test strip" for receiving the blood sample, the test strips characteristically being relatively expensive. Such measurements are often painful, cumbersome, and moderately time-consuming. The method of testing blood glucose using a test strip is generally referred to as the "finger stick" method. It specifically involves applying a drop of blood to the test strip, the test strip using molecular sieves to block molecules larger than molecular weight of about 200. The sieves consequently block, for example, large glycosylated proteins from being included in the blood glucose measurement. Due to the inconvenience and expense, many diabetic patients do not monitor their blood glucose levels as often as recommended. About 16 million diabetic patients in the United States need to regularly monitor their blood glucose levels.

A non-invasive device enabling painless and convenient monitoring of blood glucose would be of great benefit to diabetic patients. The relative ease of measurement may contribute to a more regular blood glucose monitoring regime by diabetic patients. Various attempts have been made at a blood glucose measurement device using spectroscopy. However, those attempts have generally had problems with "baseline drift" of unknown origin. It is hypothesized that the absorption method used in most spectroscopy devices for measuring glucose in the blood measures all glucose in the blood, both the bound glucose and the free glucose. For the purpose of diabetes management, measurement of the concentration of free glucose is desired. That is, the concentration of free glucose in the blood is generally recommended to be in the range of 80 mg/dL and 120 mg/dL. A diabetic patient will measure their blood glucose level to determine whether the level is within the recommended range. If the blood glucose level is outside of the recommended range, the diabetic patient will typically inject insulin to reduce the blood glucose level. Again, it is the free glucose concentration level that is relevant to determining whether the patient's blood glucose concentration is within the recommended range. Because absorption techniques may measure both free and bound glucose levels as one measurement, there may be an overstatement of the blood glucose level that results in faulty treatment by the patient. The molecular sieves of the test strip glucometers described above correct for the possibility of measuring bound and free glucose by preventing the bound glucose, with a relatively high molecular weight, from passing through the sieve.

It is notable, however, that the finger stick methods take only one measurement of the glucose concentration level in the blood and, for a series of measurements, require a series of blood samples, generally obtained by a series of finger pricks. Consequently, the finger stick methods do not offer an appealing method of continuous measurement of blood glucose concentration in the blood. Continuous measurement of blood glucose levels enable near instant recognition of abnormal blood glucose levels whereas a series of individual measurements inevitably includes periods of time where the precise blood glucose level is unknown. Thus, a diabetic patient may be better able to control blood glucose levels. It may also assist the person in adjusting their lifestyle, diet, and medication for optimum benefits. Providing the easy, non-invasive, and optionally continuous monitoring provides a great improvement in the treatment of the diabetes and allows the treatment to be tailored to the individual.

Many other blood analytes with concentrations similar to or greater than lactate and glucose are of fundamental importance; for example, hemoglobin and its sub-types, albumin, globulins, electrolytes, and others. Hemoglobin is important especially in the monitoring of anemia caused by various various factors such as HIV infection and chemotherapy. Anemia treatments need frequent monitoring of hemoglobin to assess effectiveness of various treatments such as Epoetin-Alpha therapy.

Spectrophotometry provides a useful method for determining the presence of analytes in a system. A typical spectrometer exposes a dissolved compound to a continuous wavelength range of electromagnetic radiation. The radiation is selectively absorbed by the compound, and a spectrograph is formed of radiation transmitted (or absorbed) as a function of wavelength or wave number. Absorption peaks are usually plotted as minima in optical spectrographs because transmittance or reflectance is plotted with the absorbance scale superimpose, creating IR absorption bands.

At a given wavelength the absorption of radiation follows Beers' Law, an exponential law of the form:

$$A = \epsilon C b \text{ Where: } A = \text{absorbance} = -\log_{10}(t; ).$$

t=fraction of radiation transmitted (or reflected).
$\epsilon$=molar extinction coefficient, cm$^2$/mol.
C=concentration, mol/cc.
b=thickness presented to radiation, cm.

The wavelengths of maximum absorption, $\lambda_{max}$, and the corresponding maximum molar extinction coefficient, $\epsilon_{max}$, are identifying properties of a compound. Radiation causes excitation of the quantized molecular vibration states. Several kinds of bond stretching and bond bending modes may be excited, each causing absorption at unique wavelengths. Only vibrations that cause a change in dipole moment give rise to an absorption band. Absorption is only slightly affected by molecular environment of the bond or group. Nevertheless, these small chemical shifts may aid in uniquely identifying a compound. A "fingerprint region" exists between 42 and 24 THz (1400 and 800 cm$^{-1}$) because of the many absorption peaks that occur in this region. It is virtually impossible for two different organic compounds to have the same infrared (IR) spectrum, because of the large number of peaks in the spectrum. While the peaks and valleys are the traditional features used in this type of spectrophotometry, the overall shape of the spectra may also provide useful information, especially in mathematically separating mixed spectra where more than one analyte is present.

In addition to the IR absorption bands, absorption peaks also occur in the near-IR region (700–2500 nm). Absorptions in this region are most often associated with the overtone and combination bands of the fundamental molecular vibrations of —OH, —NH, and —CH functional groups that are also seen in the mid IR region. As a result, most biochemical species will exhibit unique absorptions in the near-IR. In addition, a few weak electronic transitions of organometallic molecules, such as hemoglobin, myoglobin, and cytochrome, also appear in the near-IR. These highly overlapping, weakly absorbing bands were initially perceived to be too complex for interpretation and too weak for practical application. However, recent improvements in instrumentation and advances in multivariate chemometric data analysis techniques, which may extract vast amounts of chemical information from near-IR spectra, allow meaningful results to be obtained from a complex spectrum. Absorption bands also occur in the visible range (400–700 nm). For example, hemoglobin and bilirubin absorb strongly in this region.

Traditionally, Near Infrared Spectroscopy (NIRS) has been used to estimate the nutrient content of agricultural commodities. More recently NIRS has become widely applied in the food processing, chemical, pulp and paper, pharmaceutical, polymer, and petrochemical industries.

Invasive devices and methods of quantifying and classifying blood analytes using IR and other optical spectrophotometry methods are very commonly known. Invasive procedures are those where a sample such as blood is taken from the body by puncture or other entry into the body before analysis. Invasive procedures are undesirable because they cause pain and increase the risk of spread of communicable, blood-borne diseases. Further, after the invasive collection of body samples, these samples may need to be further prepared in the laboratory by adding water or ions to the samples to increase the accuracy of the spectrophotometry readings. Thus, these commonly known devices and methods are often only suitable for use under laboratory in vitro conditions and are too difficult to be practically applied in athletic training and military situations. It is noted, of course, that the finger stick method of measuring blood glucose concentration levels using a glucometer has been adapted for home use.

Recently, non-invasive devices for monitoring levels of blood analytes using infrared spectroscopy have been developed. For example, U.S. Pat. No. 5,757,002 by Yamasaki relates to a method of and an apparatus for measuring lactic acid in an organism in the field of sports medicine or exercise physiology. Also, U.S. Pat. No. 5,361,758 by Hall relates to a non-invasive device and method for monitoring concentration levels of blood and tissue constituents within a living subject.

Previous non-invasive devices and methods typically require time-consuming custom calibrations to account for the differences between individuals and environmental factors which cause variation in energy absorption. There are several factors that may result in variation in energy absorption; for example, environmental factors such as temperatures and humidity that may affect the equipment, and individual factors such as skin coloration, skin weathering, skin blemishes or other physical or medical conditions. This need for custom calibration to each individual makes it impractical to use previous devices on demand in training situations or at the scene of accidents. A universal or self-calibrating device that is capable of taking into account these variations would be useful.

Further, many previous non-invasive devices and methods accurately measure only a single blood analyte at a time. Most typically, the devices are designed to measure blood glucose. To measure a different analyte, the device must be reprogrammed or otherwise altered. Even with such reprogramming or alteration, the devices may not typically measure the results of two or more analytes at the same time without significant inaccuracies. Each analyte in the blood sample contributes a unique absorption pattern to the overall infrared spectrum, governed by the unique set of molecular vibrations characteristic of each distinct molecular species. The infrared spectral range extends from 780 nm to 25,000 nm and is commonly subdivided further into the near-infrared and mid-infrared regions. Most devices obtain an measurement of an analyte by using only a small portion of the IR spectrum reflecting the particular analyte of interest. In those devices that do attempt to use a wider spectrum to obtain multiple analyte readings, relatively ineffective methods are used to separate and account for multiple analyte spectral interferences, leading to decreased accuracy. Thus, there exists a need for a device that may successfully use a wider spectrum to accurately and simultaneously isolate and determine the concentrations of multiple analytes.

IR spectroscopy typically involves radiating light onto a portion of tissue for either transmission through the tissue or reflection from the tissue. The transmitted or reflected radiation is then analyzed to determine concentrations of analytes. However, the radiation that is transmitted or reflected is not just transmitted through or reflected from the blood, but instead includes transmissions or reflection from the skin, subdermal tissue, and blood. Thus, the received radiation is a mixture of absorption signals from skin and tissues and blood. The signals contributed by the skin and tissues make it difficult to accurately measure the presence of blood analytes. These signals need to be separated to eliminate the effects of skin and tissue in order to measure the analytes in the blood. Previous non-invasive devices and methods were unable to separate blood-related readings from body tissue readings. Therefore, there is a need for a device capable of separating the blood-related component of the signal from the tissue component.

One method of achieving the separation of a blood-related component of the signal is to accept only the portion of the mixed signal which has a pulse synchronized with the heart pulse, known as a pulsatile technique or synchronous detection. The pulsatile signal is the time varying portion of the whole signal that is synchronized with the heart beat. This method presumes that the pulsations come from the movement of arterial blood or closely related volume and allows a signal associated with the blood to be separated from that of tissue. The synchronous method is widely used for separating blood-related components in pulse oximeters.

Another possible method for achieving separation of the blood related components of the signal from tissue and skin related components uses a hematocrit-type method to determine the portion of the signal associated with the blood. The hematocrit is the proportion, by volume, of the blood that consists of red blood cells. The hematocrit is typically measured from a blood sample by an automated machine that makes several other measurements at the same time. Most of these machines do not directly measure the hematocrit, but instead calculate it based on the determination of the amount of hemoglobin and the average volume of the red blood cells. Using a hematocrit method generally is faster than using a synchronous method because there is no need to wait for heart beats. Further, there is less signal loss associated with hematocrit methods than with the synchronous method, the synchronous method removing some blood associated signal unnecessarily.

Finally, many non-invasive devices for in vivo monitoring of blood analyte concentrations do not allow for an ambulatory application. They typically utilize permanent equipment set up in a laboratory or other test site, which makes it impossible to use while away from the laboratory or other test site. Thus, there is a need for a device that may be easily transported and used away from the laboratory. The device would preferably not interfere with the user's normal functioning and would greatly increase the utility and range of analyte concentration monitoring beyond the laboratory setting.

SUMMARY OF THE INVENTION

The present invention provides an improved apparatus and method for the rapid, non-intrusive determination of the concentration of blood analytes. In one embodiment, it provides a portable tabletop unit for measurement of blood analyte concentrations where the subject may walk up to the device for measurement from a body part, such as a finger. However, there are many situations where blood analyte measurement must be done outside of a domestic or laboratory environment. Thus, another embodiment of the present invention provides a portable system which may be positioned on body tissue and transported on the user's person. Features such as small size, a wireless sensor, battery operation, portability, and downloadability demonstrably increase the utility and range of the analyte measurement apparatus of the present invention beyond the hospital or laboratory setting.

The present invention also provides a method and apparatus with increased sensitivity and accuracy. A problem encountered in the area of blood analyte measurement via IR spectroscopy is accuracy and drift. In general, other analytes and various other substances present interfere with the IR measurement of the desired analyte. These analytes vary in concentration and thus vary the IR spectrum in the regions being used to determine specific analyte concentration. The present invention corrects for all other analytes with concentrations sufficient to interfere in the determination of the concentration of the analyte or analytes of interest. Measuring the entire visible and IR spectrum provides enough data to simultaneously determine all of the analytes and thereby compensate for any accuracy or drift problems their concentration may cause in measuring the concentration of the analyte(s) of interest. Data processing using orthogonal functions is used to accomplishing this task. Other properties of blood may also effect the IR measurement of the desired analyte. For example, turbidity of the blood, as may be caused by elevated white cell count or high blood lipids, may affect the measurement. These factors appear in the spectra and are compensated for by the present invention. The analyte measurement apparatus of the present invention is sufficiently sensitive to detect blood glucose or lactate with accuracy within, approximately, 10% of the level actually present, and may do so in a short period of time (e.g. 5 seconds or less). Due to the non-intrusive nature of the measurement and its relative rapidity, it is also possible to monitor blood analyte levels essentially continuously.

The blood analyte measurement apparatus of the present invention includes a radiation source for generating and transmitting a spectrum of radiation onto a portion of tissue (for transmission therethrough or reflection therefrom), one or more sensors for detecting the radiation either transmitted through or reflected from the tissue over a broad spectrum and generating an output in response to the detected radiation, and a processor for receiving output from the sensors to determine the concentration of blood analytes in the portion of tissue. In a preferred embodiment, the apparatus also makes use of a mounting device to position the radiation source and the sensors relative to a portion of tissue so the one or more sensors may receive a substantial portion of the radiation produced by the radiation source and transmitted through or reflected by the portion of tissue. In a further preferred embodiment, the information regarding absorption of the radiation is then algorithmically processed to clarify the signal(s) of the desired blood analytes. Thus, the invention, in a typical configuration, includes a sensor module which is preferably attached to an earlobe, a pocket monitor for immediate readout and data logging, and a data link to a PC for long term storage and compilation of data. Thus, blood analyte levels may be continuously monitored without the constraints of attachment wires or bulky apparatus.

The blood analyte sensor module is integrated as much as possible to reduce the size and weight. In one embodiment, the sensor module is completely self-contained. The sensor module illuminates the measurement site with a built-in radiation source tailored to the spectral region of interest. The radiation source and the sensors are each positioned on a chip. The radiation source may be integrated onto a custom chip in transmission mode, or onto the same chip as the sensors in reflection mode. That is, when it is desired to receive and interpret radiation transmitted through the tissue, the apparatus is working in transmission mode and the radiation source is positioned on a chip separate from the chip on which the sensors are positioned. In contrast, when it is desired to receive and interpret radiation that is reflected from the tissue, the apparatus is working in reflection mode and the radiation source may be positioned on the same chip as the chip on which the sensors are positioned. Preferably, the radiation source is a thermal radiator made up of tungsten or tantalum positioned over a reflective heat shield.

The blood analyte measurement apparatus also optionally includes a focusing device for focusing the radiation from the radiation source onto a point on the tissue. A fresnel lens, for example, works well in this capacity. The apparatus also optionally includes a collimator to compensate for the scattering that typically occurs when the radiation passes through tissue. The beam divergence of the collimator, if used, should be approximately 5 degrees or less.

A filter may also be included to separate the radiation received by the sensors into various wavelengths subsequent to collimation. The preferred filter for this separation is a Fabry-Perot narrow band interference filter comprising a dielectric film between two metal films, where the dielectric film has a graded thickness running from a short wavelength end with a thickness of about 100 nm to a long wavelength end with a thickness of about 2.5 microns. Between the narrow band interference filter and the sensors is a planarizing layer. The spectrophotometer bears sensors which are preferably sensitive to radiation from wavelengths of about 700 nm to about 2500 nm.

The sensors within the sensor module are divided into two groups: direct silicon sensors sensitive to radiation of a wavelength range from about 0.4 to 1.1 microns, and infrared sensors sensitive to radiation of a wavelength range from 1 to 10 microns. Using both types of sensors, the apparatus of the present invention preferably uses an array of approximately 1024 elements, for an overall filter passband of about 0.22 percent of its center wavelength or frequency. The direct silicon sensors may be, for example, either photodiodes or charge coupled devices. A charge coupled device array made up of multiple elements sensitive to differing portions of the wavelength range is preferred. The infrared sensors making up the rest of the array may, for example, be extrinsic silicon, pyroelectric, photoconductor, or thermocouple sensors. Thermocouples comprising two layers of metal with an additional layer of gold black are preferred, where the two metal layers may be either nickel-chromium alloy on nickel-copper alloy, for example. The sensor module may include a replaceable, rechargeable battery and use a unique ID code if desired.

A processor is provided for processing the output from the sensors. If desired, an RF transmitter or other device may be provided for wirelessly transmitting the signals from the sensors to the processor. This processor is preferably a CMOS microprocessor, which uses a Boolean algorithm to process the output from the sensors. Various processing algorithms are used to enhance the value of the data obtained from the sensors. The blood analyte measurement apparatus may also include a display, typically a liquid crystal display, for the immediate display of data to the user. The data may be downloaded to a computer or other device via an I/O port, typically an RS-232 port.

The present invention also discloses a method for measuring the concentration of one or more blood analytes in a portion of tissue with a non-invasive measuring apparatus. The method involves positioning a portion of tissue approximately adjacent one or more sensors and a radiation source, exposing the tissue to radiation from the radiation source, detecting radiation transmitted through or reflected from the tissue with the one or more sensors, generating a signal from the one or more sensors in response to the detected radiation, communicating the signal to the processor, and finally interpreting the signal communicated to the processor to determine the concentration of one or more blood analytes. Preferably, the method of the present invention also includes the step of displaying the results so they may be perceived by the user.

The preferred tissue exposed to the radiation in the method is either an earlobe or a finger. Preferably, the positioning of the tissue is carried out so that the sensors and the radiation source have minimal or no contact with the tissue itself. While any analyte which has infrared absorption may be measured by this method, specific examples are lactate/lactic acid, glucose, insulin, ethanol, triglycerides, albumin, proteins, hemoglobin, immunoglobulins, cholesterol, and urea.

An important aspect of the present invention is the interpreting of the signals communicated to the processor by an algorithm. One type of algorithm used to interpret this data is linear regression. A more preferred algorithm makes use of orthogonal functions. The concept is to use the reference spectrum for each blood analyte as basis functions and determine a weighting function or functions that create an orthogonal set. This permits easy separation algorithms for mixed spectra. The use of algorithms is very helpful for self-calibrating to eliminate data artifacts caused by individual variation in tissue character.

The least squares method of orthogonal functions is preferably used to separate the concentrations of the individual analytes from the total spectrum measured. This is also referred to as "principle component analysis" and is similar to "Fourier series decomposition." Separating the various analyte concentrations is statistically challenging because of an overlap of the spectra which causes interactions and cross-coupling. Trying to evaluate one analyte concentration is affected by the other overlapping concentrations. The orthogonal decomposition is a mathematical way of processing the overlapping concentrations so that they are non-interacting.

Beers' law, described above, may be used to describe blood as a series where each term in the series represents aborbance of one of the blood analytes. As an example, if the blood contains fixed known concentrations of the analytes, and if the absorption spectrum is known for each of these analytes, then the composite spectrum CS can be calculated directly. The method of the present invention measures the composite spectrum and the reference spectra. Concentration coefficients are determined using the orthogonal function decomposition.

DETAILED DESCRIPTION OF PREFERRED EMBODIMENTS

Figure 1:
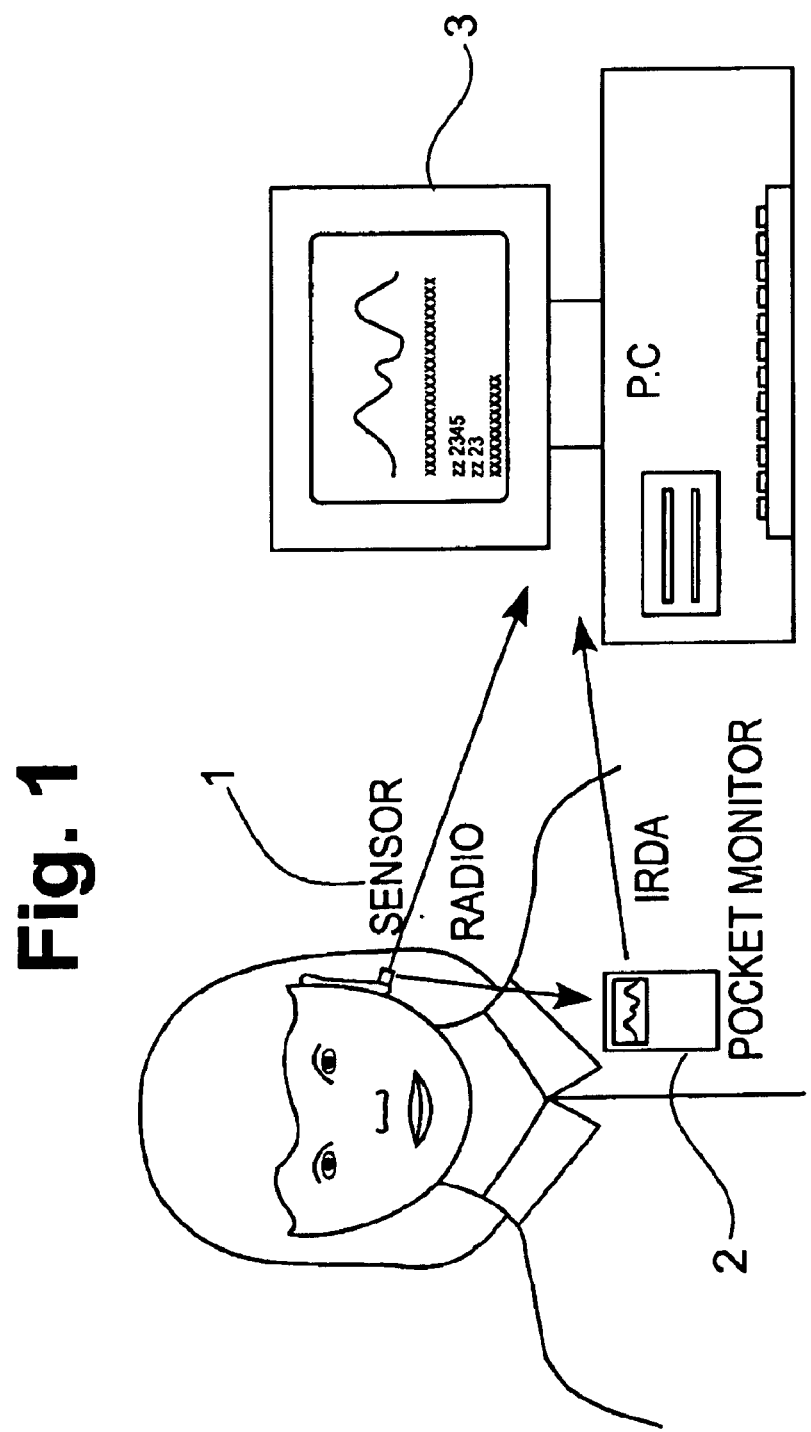
FIG. 1 is a drawing illustrating the overall concept of the non-invasive blood analyte micromonitor.

The following detailed description is to be read with reference to the drawings, in which like elements in different drawings have been given like reference numerals. The drawings, which are not necessarily to scale, depict selected embodiments and are not intended to limit the scope of the invention.

One preferred embodiment of the present invention is a blood analyte measurement apparatus for measuring the concentration of blood analytes outside of a laboratory setting. The blood analyte measurement apparatus utilizes a sensing unit 1, such as a micromonitor sensor module, that is preferably small and inobtrusive and does not interfere with a user's normal functioning. FIG. 1 shows an embodiment of the analyte measurement apparatus, with the sensor module 1, support hardware such as a pocket monitor 2 and an optional computer interface 3. The sensor module contains a small spectrophotometer, which comprises two sensor arrays and a custom graded narrow band interference filter. The sensor module also preferably contains an RF radio transmitter to broadcast the data produced by the sensor, typically only over a limited range, and a rechargeable battery as well as custom optics. The sensor module may be used in an ambulatory application where the user simply clips the sensor module 1 onto an appropriate tissue region, puts the pocket monitor 2 in a pocket/purse and goes about their business. The pocket monitor display give the user immediate data, and stores the data, optionally for later downloading to a computer 3.

Figure 2:
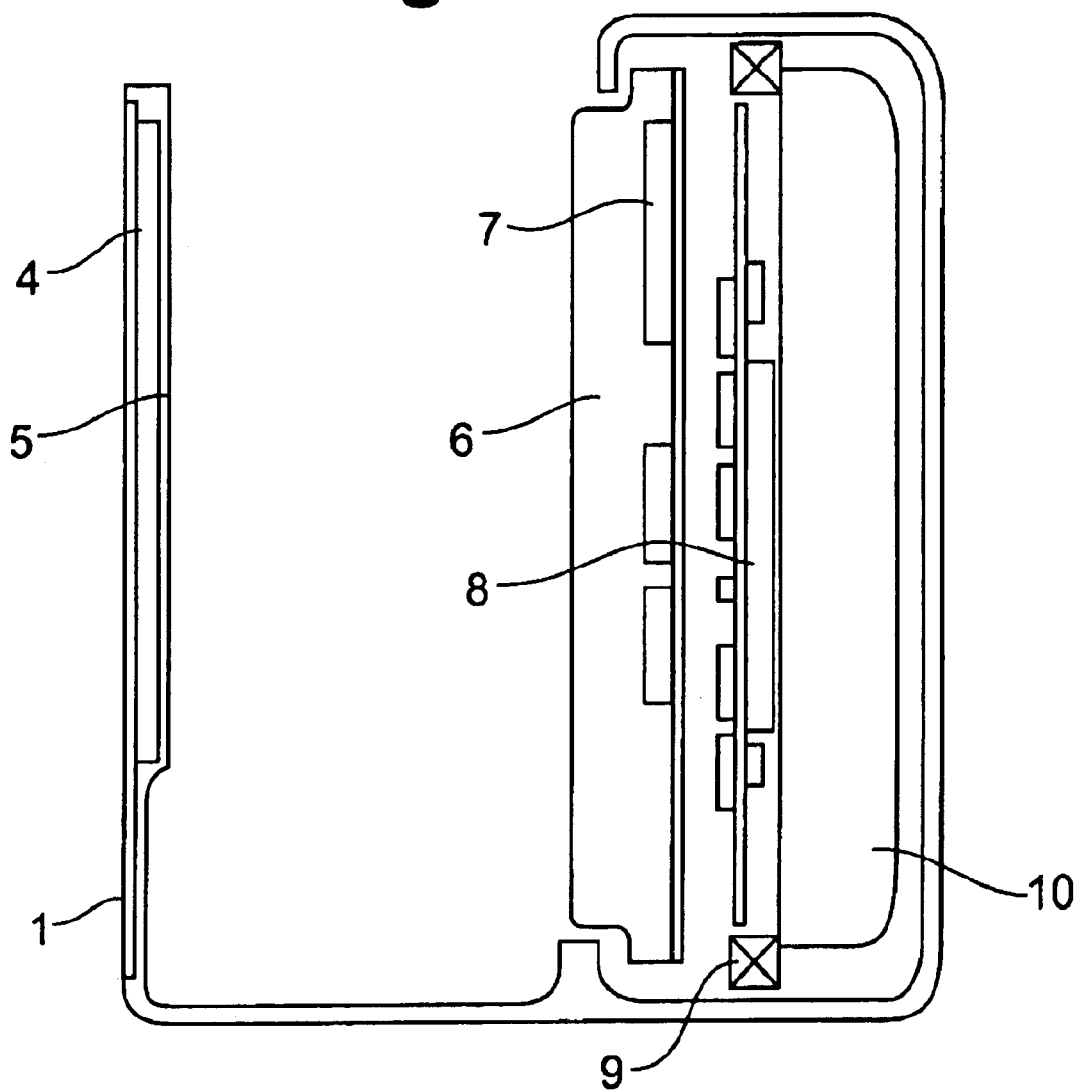
FIG. 2 is a drawing illustrating one possible construction for the sensor module.

The micromonitor sensor module 1 shown in detail in FIG. 2 is integrated to reduce its size and weight. The sensor module may also be completely self-contained. As shown, the sensor module is configured for attachment to the user's ear lobe, the ear lobe being the preferred measurement site. Of course, sensor modules intended for attachment to other measuring sites may be configured differently. The target sensor volume is preferably 5 to 10 cc for lactate monitoring, and 1 to 2 cc for glucose monitoring. The sensor module, as shown, is configured to illuminate the measurement site and to receive the reflected radiation from the measurement site. The configuration of the sensor module or modules may vary for receiving transmitted radiation from the measurement site. The sensor module of FIG. 2 illuminates the measurement site with a radiation source 4 configured to generate radiation in the spectral region of interest. As wide a spectrum as practical is generated, preferably with a wavelength range as wide as 0.4–10 microns. Adjacent to the radiation source 4 are source optics 5 which help to direct and focus the radiation. As shown, the sensor also has collimator optics 6, as well as an integrated narrow band filter, and individual sensors. The individual sensors may be, for example, thermocouple sensors and/or charge couple device (CCD) sensors 7. The sensors are preferably built directly onto a CMOS chip 8. If desired, each sensor module may have a unique ID code.

The sensor module also preferably contains an RF radio transmitter 9 to broadcast the data received by the sensor as reflection or transmittal of the radiation, that is the transmitted or reflected radiation from the measurement site, and a rechargeable battery 10 as well as custom optics. Typically, only a weak RF source is provided since the signal is generally broadcast over only a few feet. Preferably, as much functionality as possible is integrated onto the custom CMOS chip 8 (e.g., preamplification, data processing, IR data output). The sensor module may analyze the blood spectra, that is illuminate the measurement site and receive the transmitted or reflected radiation therefrom, at fixed time intervals, such as once every minute, and is capable of running an analysis in less than five seconds. A further preferred embodiment of this blood analyte measurement device includes a non-invasive sensor module that utilizes infrared spectrophotometric techniques.

A narrow-band interference filter 11 is used as a color separation device in the sensor module. This type of filter is preferred due to its small volume, minimal needs for optics to collimate the radiation, and inherent compatibility with integrated circuit processing techniques. A very small spectrophotometer results when this filter is combined with a CMOS chip bearing an array of sensors.

The radiation (typically, visible and IR or near-IR light) sources 4 of the sensor module may be integrated onto a different chip from that bearing the sensor array for transmission mode or onto the same chip for reflection mode. In one embodiment, the radiation source comprises a series of incandescent elements integrated onto a silicon chip. Existing tungsten/tantalum technology (used in fusible link type EE Prom's) may be combined with Micro-Electro-Mechanical Systems (MEMS) to form an array of radiation sources tailored to the specific needs of this spectrometer. MEMS technology is the integration of mechanical elements, sensors, actuators, and electronics on a common silicon substrate through the utilization of microfabrication technology.

Figure 3:
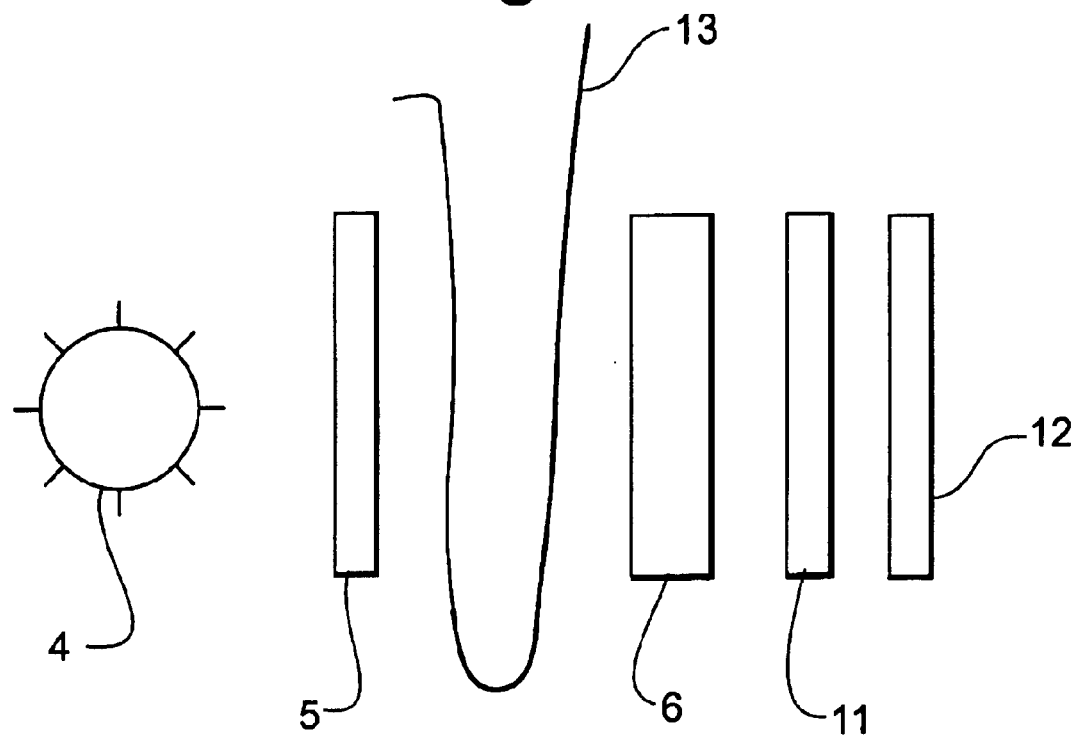
FIG. 3 is a drawing illustrating the positioning of the basic components of the sensor module with respect to an ear lobe.

FIG. 3 illustrates the relationship between the sensor components and a portion of tissue, an ear lobe 13, which is a preferred measurement site. These components are the radiation source 4, the source optics 5, the light collimator 6, the narrow band filter 11, and the integrated sensors 12. The ear lobe is a rich source of blood, and attachment of the sensor module thereto meets the ambulatory monitoring goals to be unobtrusive and not interfere with normal user activity. FIG. 3 shows a configuration where radiation is transmitted through the ear lobe 13, rather than reflected from it. This configuration requires components on both sides of the ear lobe, but generally uses the available radiation more efficiently than a configuration where the radiation reflected from the ear lobe is sensed. A configuration for sensing radiation reflected from the ear lobe, not illustrated, includes the same components as the configuration illustrated in FIG. 3 (a radiation source, source optics, a light collimator, a narrow band filter, and integrated sensors) where all of the components are positioned on one side of the ear lobe. The reflection mode generally requires a stronger radiation source than the transmission mode.

FIG. 3 also illustrates the positioning of the source optics 5. A cylindrical Fresnel style lens is preferred for the source optics for the analyte measurement apparatus. The source optics focus the radiation from the radiation source onto a point at the center of the ear lobe. A Fresnel lens also has a relatively small volume. Once the radiation has been transmitted or reflected from the measurement site, it is run through a collimator 6, followed by a narrow band filter 11, and then finally is received by the integrated sensors 12.

The integrated sensors are directly adjacent to the narrow band filter 11 and consist of two types of infrared detectors sensitive to discrete portions of the spectrum: direct silicon sensors sensitive to radiation of a wavelength range from about 0.4 to 1.1 microns, and infrared sensors sensitive to radiation of a wavelength range from 1 to 10 microns. Using both types of sensors, the apparatus of the present invention preferably uses an array of approximately 1024 elements, for an overall filter passband of about 0.22 percent of its center wavelength or frequency. The direct silicon sensors may be, for example, either photodiodes or charge coupled devices. A charge coupled device array made up of multiple elements sensitive to differing portions of the wavelength range is preferred. The infrared sensors making up the rest of the array may, for example, be extrinsic silicon, pyroelectric, photoconductor, or thermocouple sensors. Thermocouples comprising two layers of metal with an additional layer of gold black are preferred, where the two metal layers may be either nickel-chromium alloy on nickel-copper alloy, for example.

Figure 4:
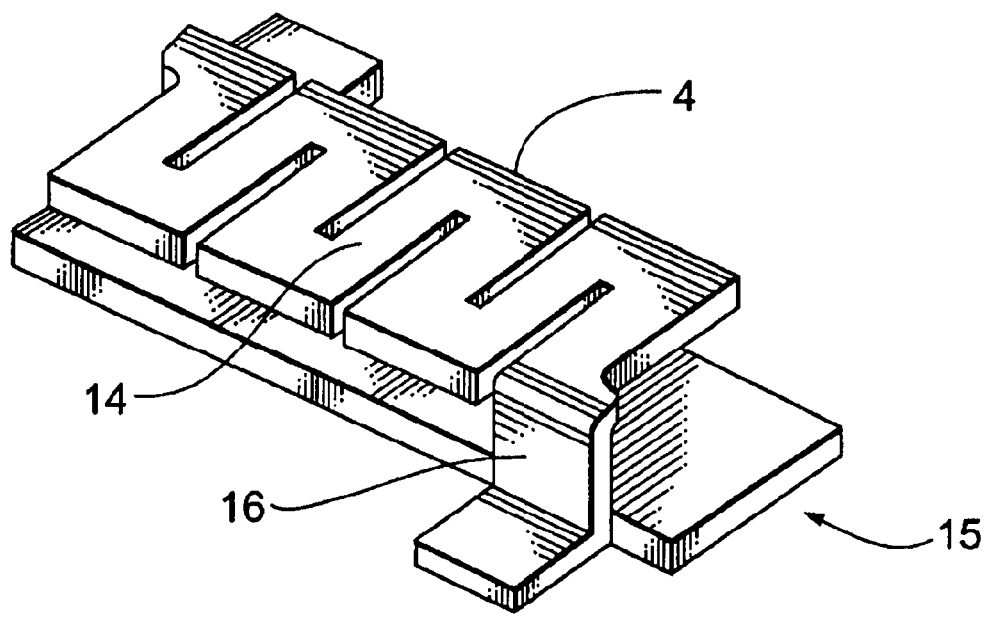
FIG. 4 is a perspective view of an integrated radiation source element.

The integrated radiation source illustrated in FIG. 4 provides rapid turn on and off times, a tailored emission spectrum, and may be configured to a relatively small size. Preferably, the radiation source 4 utilizes a high melting temperature metal such as tungsten or tantalum to form a thermal radiator 14. The radiator is spaced above a silicon wafer by MEMS techniques and supported by the electrical connections and/or auxiliary supports 16. If serpentine construction is used, the resistance may be adjusted to a convenient value such that it may readily match driver characteristics.

Presuming that sufficient thermal isolation is achieved, the element is allowed to become very hot. A metal reflector layer 15 on the wafer under the thermal radiator element 14 boosts emission efficiency and reduces the heat load to the silicon wafer. The optical color of the emission is set by the temperature of the element, and optical power by the emitting area. Using an array of such elements, each with a different temperature and area, the total emission spectrum may be adjusted to be reasonably flat over the spectrum of interest.

The integrated radiation source allows control over the heat leak associated with the supports. The heat leak may be adjusted to achieve almost any desired turn on and turn off times of the light. Each element, when hot, has a relatively small heat capacity, permitting switching times in the millisecond range without exorbitant power expenditure. With rapid turn on and turn off times, an electronic "chopper-wheel" with modulation frequency in the range of 1 Khz, may be used to reject unwanted background signals.

Heat transfer calculations are provided using tungsten (3370° C. melting temperature) film 1000 angstroms thick. A hot resistance in the range of 10–100 ohms is obtained with a resistor length of 10000 to 30000 squares, well within IC capability. An element temperature of 2000° C. emits 2 to 50 mw radiant energy centered at about 1.5 micron wavelength using photolithographic line widths of 1–5 microns. Heat loads due to supports, electrical connections, and other losses may be held to the range of 1–10 mw. Air conduction loss is eliminated by evacuating the hot zone. The small element heat capacitance the order of 30–770 njoules/° C. results in thermal time constants of 0.2–4 milliseconds. Tantalum (2996° C. melting temperature) gives similar results but has less severe inrush currents than tungsten. Thus, an integrated radiation source with a total power dissipation in the range of 10–100 mw, battery compatible resistance, millisecond response times, and compatibility with IC processing is clearly possible using tungsten or tantalum.

Figure 5:
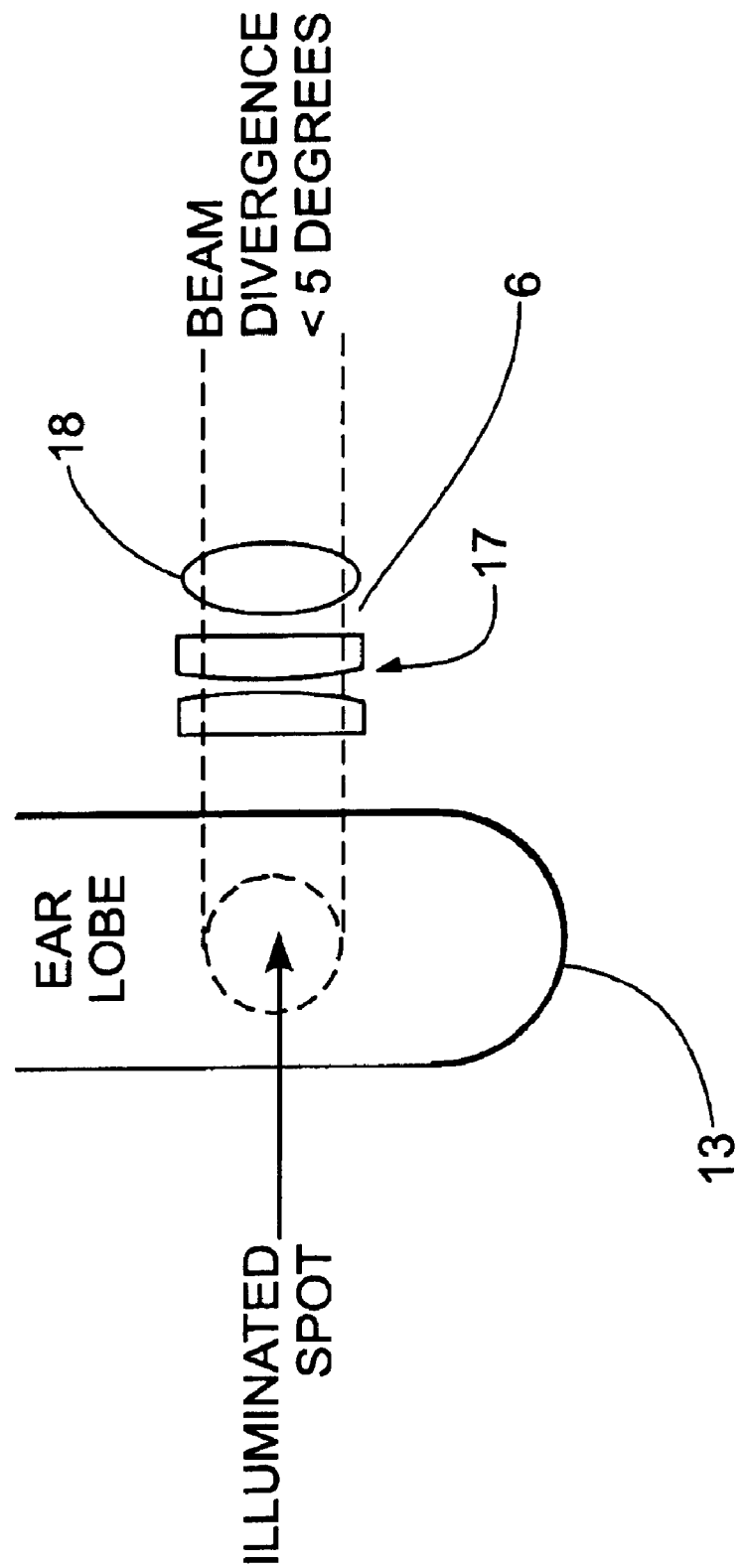
FIG. 5 is a drawing illustrating the operation of the collimator.

The ear lobe 13 is shown in both FIG. 3 and FIG. 5. The analyte measurement device of the present invention compensates for complications of IR spectroscopy inherent in measurement through skin and tissue. The ear lobe infrared absorption spectrum corresponds roughly to two layers of skin; one on the backside of the ear and the other on the front side. The transmission of light through skin is fairly complicated. The skin includes a stratum corneum, about 10 microns thick, an epidermis, about 100 microns thick, and a dermis, about 3 mm thick. The incident radiation suffers a 4% to 7% reflection at the stratum corneum due to change in index of refraction (1.0 for air to 1.55) over the whole spectral range up to 3 microns wavelength for both white and black skin. The stratum corneum also contributes to scattering since it is not flat, and has a certain roughness. The chromophores of the epidermis especially melatonin determine attenuation in the visible range in this layer. Psoriatic skin may also be a significant interfering factor, perhaps requiring clear lipophilic liquids to enhance light penetration in some individuals. In the dermis, blood chromophores Hb, $HbO_2$ and biliruben are the primary absorbers. Scattering by collagen fibers in the dermis is a strong influence on transparency. Attenuation exceeding 90% may be expected. An optical window exists between 0.6 and 1.8 microns wavelengths where the skin is most transparent. While the ear lobe is a preferable portion of tissue for the measurement site, the present invention is by no means limited to this particular tissue.

FIGS. 3 and 5 both illustrate the use of a collimator 6 with the analyte measurement device as well. The radiation received from the illuminated ear lobe 13, either by transmission or reflection, may be scattered. The narrow band filter works more effectively when the radiation has been collimated. A beam divergence of 5 degrees or less is preferred. One method is to use a standard condenser 17 and projector 18 lens arrangement, as illustrated in FIG. 5. Considering the source of radiation for the collimator to be the spot illuminated inside the ear lobe, this spot is imaged by the condenser lens 17 onto the projector 18 lens aperture, and projected in a beam. The scheme illustrated in FIG. 5 has a minimum volume of about 2 cc. Microlens arrays may be used to reduce the volume. For example, an array of microlenses may be configured at a fraction of a cubic centimeter.

Figure 6:
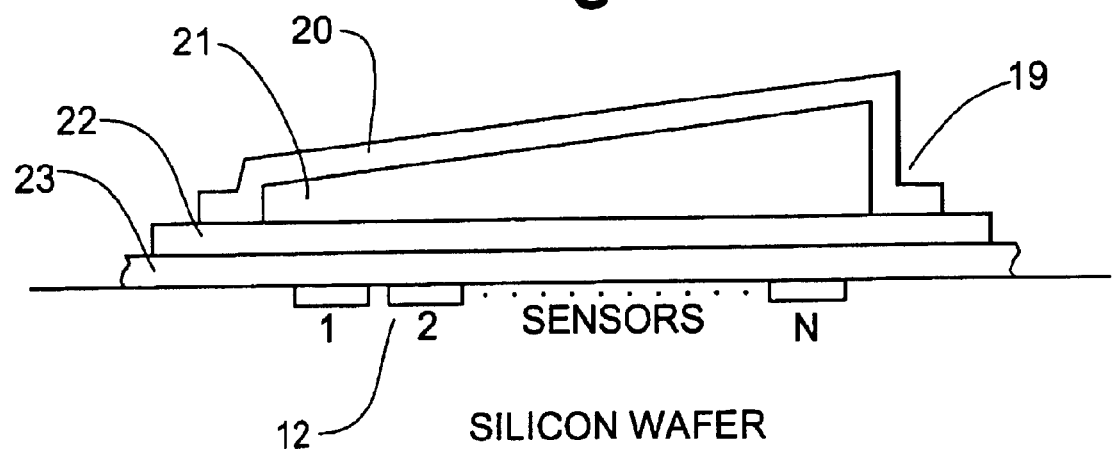
FIG. 6 is a drawing illustrating the layered components of a narrow band filter integrated directly onto a sensor chip.

FIG. 6 portrays a preferred narrow band filter. The narrow band filter separates the wavelengths of radiation transmitted through the tissue at the measurement site and directs the various wavelengths to the sensing array, which is preferably a linear array of elements. The sensors at one end of the array sense only radiation from one end of the spectrum, for example 0.4 microns, while the sensors at the other end of the array sense only radiation from the other end of the spectrum for example 10 microns. Using a linear graded filter, each sensor measures a different color, with color varying linearly with sensor position. A Fabry-Perot narrow band interference filter 19 with a graded dielectric thickness is preferred, where the dielectric film has a graded thickness running from a short wavelength end with a thickness of about 100 nm to a long wavelength end with a thickness of about 2.5 microns. Between the narrow band interference filter and the sensors is a planarizing layer. The spectrophotometer bears sensors which are preferably sensitive to radiation from wavelengths of about 700 nm to about 2500 nm. FIG. 6 shows a preferred form of filter, a metal-dielectric-metal sandwich.

The vertical dimension of the dielectric is a quarter wavelength. Additional layers may be used to suppress higher order resonance modes. The filter may be fabricated on a separate substrate and then affixed to the CMOS chip. Since the sensor array may be only one cm long, a separate filter is manageable. The allowable separation between filter and sensor element is determined by the amount of optical cross-talk tolerable between adjacent sensors. For example, if the sensor dimension is approximately 10 microns and the incoming light has a divergence of 5 degrees, then a separation of 25 microns (1 mil) would result in up to 22% cross talk between adjacent elements due to the parallax effects. If a larger separation or lower cross talk is needed, then the incoming light may be better collimated.

FIG. 6 shows the narrow band filter integrated directly onto the CMOS chip 12, rather than as a separate substrate. Compared to the example above, filter-to-sensor spacing is very small, and cross talk between adjacent elements due to parallax is less than 10% for the layer thickness' used. With typical semiconductor processing, a planarizing layer may be preferable to accommodate the filter. The first partially transmitting metal layer 22 of the optical filter is then placed on the planarizing layer 23, followed by the dielectric layer 21 and then the top partially transmitting metal layer 20. A wide range of pass band widths may be obtained. Such a filter typically resonates at ¼ wavelength, corresponding to the dielectric thickness. Hence, typical dielectric thickness is 100 nm at the short wavelength end and 2.5 microns at the long wavelength end, for the preferred spectral range of 0.4 to 10 microns. Typically, most metals, e.g. gold or aluminum, are partially transmissive at layer thicknesses of 500 to 1000 angstroms. The tapered dielectric layer may be readily fabricated using fixturing (i.e. using a moving aperture) with standard semiconductor equipment. The expected thicknesses and materials may be patterned if desired by standard semiconductor processes.

The sensing array operates over a wide wavelength range of 0.4 to 10 microns. Silicon sensors are sensitive to radiation only over a wavelength range of about 0.4 to 1.1 microns. Beyond 1.1 microns, silicon is generally not useful as a radiation sensor and other methods than direct silicon sensing must be used. Two kinds of arrays are preferably used in the present invention, a direct silicon photo-sensing array and a thermocouple array. Over its range, silicon generates a much stronger signal than other sensing means. The rest of the wavelength range, from 1 to 10 microns, is sensed by the thermocouple array.

Figure 7:
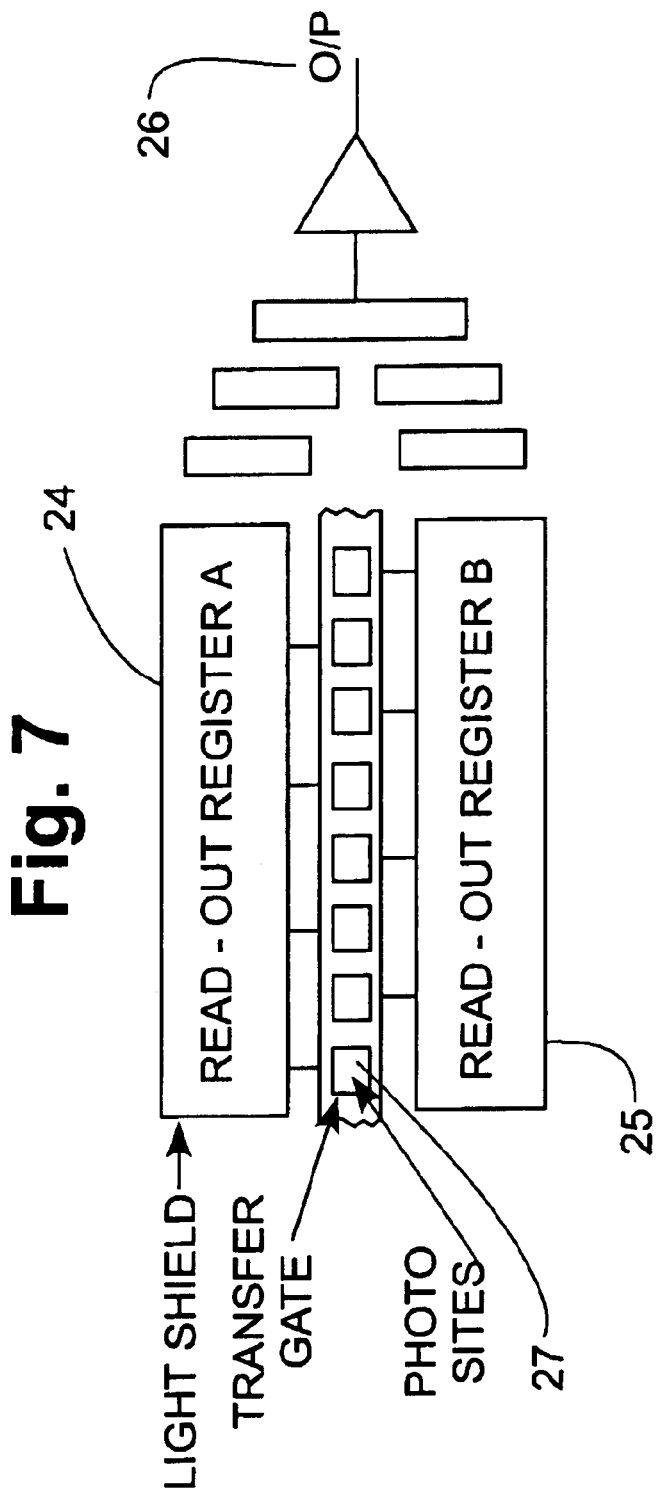
FIG. 7 is a drawing illustrating the layout of the sensor circuit and related components.

Both photodiodes and CCDs may be used for direct silicon sensing. The present invention uses CCDs because of their very large dynamic range (more than 1000:1), very low noise capability, easy handling of the small analog signals, inherent CMOS (Complementary Metal Oxide Semiconductor) compatibility, and high quantum efficiency (in the range of 0.5%). FIG. 7 illustrates a preferred CCD structure 24 for use in the present invention. The CCD may be viewed as a collection of MOS capacitors that collect photo-induced charges over a controlled integration time, then transfer the collected charges into readout registers 25 (also CCDs) which shift the data serially to an output port 26 where the analog signal is connected to an analog-to-digital converter. Photo-sites 27 are indicated in the figure with radiation impinging on the silicon through transparent poly-silicon electrodes. Various clocking schemes (e.g. two, three and four phase) may be used, depending on the geometry.

Figure 8:
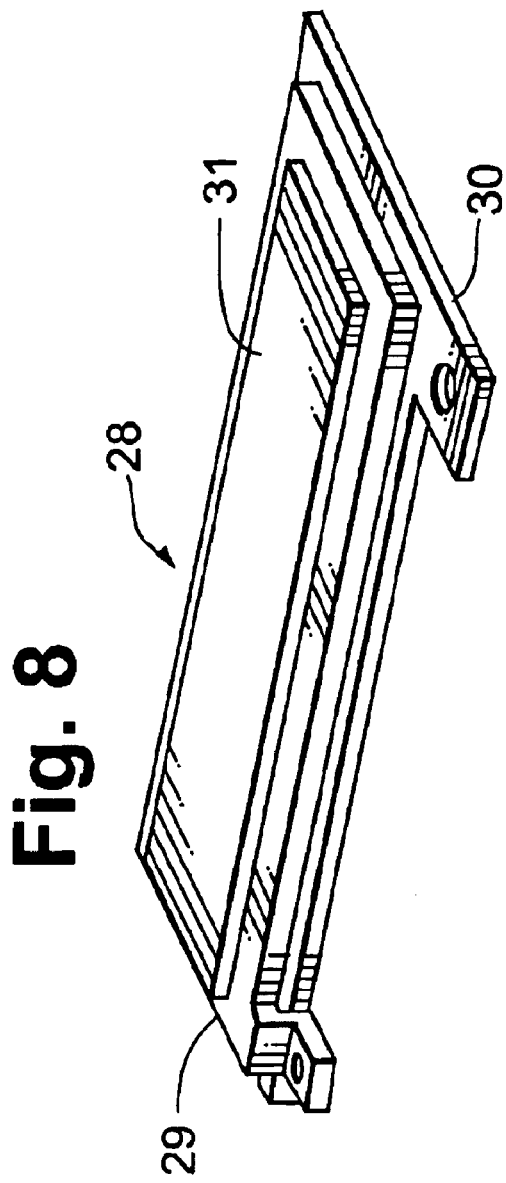
FIG. 8 is a perspective view of the thermocouple sensor cell.

FIG. 8 illustrates a thermocouple IR sensor cell 28. A variety of devices may be utilized for sensing over the IR part of the range (1 to 10 microns): extrinsic silicon, pyroelectric sensors (such as $LiTaO_3$), various photoconductors, and thermocouples, for example. The preferred embodiment of the present invention uses thin film thermocouple sensors. D*, the normalized detectivity figure, may be very high in integrated thermocouples, as high as $10^{16}$. Thin film thermocouple sensors are very compatible with IC processing and may be patterned using standard photolithographic techniques. The sensitivity to infrared energy is constant over the entire IR range from about 0.7–50 microns. The signal levels are good at 63 $\mu v/°$ C. with very low source impedance, since they are metal films. In a preferred embodiment the two metal layers of the thermocouple are nickel—chromium 29 and copper—nickel 30 alloys, as shown, with an additional layer of about 60 $\mu g/cm^2$ of gold black 31. The thermocouple sensor is thermally isolated from the substrate and exposed to the incident radiation. The cold junctions, not shown, are thermally connected to the substrate as a heat sink and shielded from the light. Additional layers may be used to connect several thermocouples in series to produce larger signals. The thin film thermocouples have a low heat capacity which produces fast response times of about a millisecond. This fast response time allows use of an amplifier tuned to the "chopper" frequency to reduce unwanted background signals. In an alternative embodiment, 2D thermal imaging may be used. An array of such elements are placed on the photo sites 27 of FIG. 7 and inject charge into the CCD.

A total of 2048 sensor elements are used to read 1024 band width increments similar to those disclosed by Hall and Pollard. Hall J. W. and Pollard A., Near-infrared Spectrophotometry: A New Dimension in Clinical Chemistry. Clin. Chem. 38, 1623 (1992). See also Hall et. al, U.S. Pat. No. 5,361,758, the disclosure of which is hereby incorporated by reference. The 1024 band increments are spread over the wavelength range of 0.4–10 microns. The passband width is expressed as a percentage rather that an absolute wavelength width. Dividing the wavelength range from 0.4–10 microns into 1024 equal percent age increments results in a pass band of 0.22% wavelength.

This corresponds to 162 wavelength "slots" for the visible range (0.4 to 1.1 microns) and 862 "slots" for the IR range (1.1 to 10 microns). Using two sensors per "slot" results in 2048 elements (324 for visible and 1724 for IR). Holding the chip size to one centimeter length results in a sensor element length of about 5 microns. A larger sensor length requires a staggered arrangement. The sensing arrays are made as wide as practical, perhaps 100 microns or more, to maximize sensitivity. The wavelength of the incident light is measured along the direction of propagation, not laterally, so that sensors may have lateral dimensions smaller than a wavelength and still sense the radiation. Using absorbing layers like gold black, radiation is absorbed in layers less than a wavelength thick.

The measurement accuracy of the present invention is quite high. Each component shown FIG. 3 has a characteristic that is strongly dependent on wavelength. To achieve the desired accuracy (e.g. 10% for glucose) these dependencies must be accounted for. Integrated radiation sources may easily have an emission spectrum that varies by a factor of 10 or more over wavelength range. This variation is partially compensated for by the design of the emitting array. Use of the narrow band filter with constant percentage passband significantly compensates at the IR end of the spectrum.

The ear lobe has absorbances that are strongly wavelength dependent and have both skin tissue and blood components. The analyte measurement device of the present invention uses an automatic compensation scheme to account for the varying skin dependencies among individuals. In one embodiment, a ratiometric technique against a known spectral shape component such as water or albumin yields suitable correction factors. The source optics, collimator optics, narrow band filter and sensor wavelength dependencies are calibrated and thereby taken into account.

Non-invasive glucose monitoring in diabetic patients has shown a more than 50% variation of transmittance in some cases at 900 nm for glucose over the physiological range (2.7 to 27.7 mmol/L). Achieving a glucose measurement accurate to within 10% thus implies a transmittance accuracy of at least 2%. To achieve this accuracy, absorbance measurements accurate or repeatable to 0.1% give a sufficient margin. A 13 bit analog to digital converter is therefore recommended. In a preferred embodiment of the present invention, a 16 bit integrated converter is used.

The present invention uses radiation either reflected or transmitted through tissue at the measuring site, including skin, sub-dermal tissue, and blood, so the received signal is a mixture of signals from blood and tissue. One embodiment of the present invention achieves the separation of the blood-related component of the signal from the tissue component of the signal by accepting only the portion of the mixed signal which has a pulse synchronized with the heart pulse. This presumes that the pulsations come from the moving arterial blood or closely related matter and thus allows a signal associated with the blood to be separated from that associated with the tissue. Pulse oximeters, for example, operate using this method. In a preferred embodiment, hematocrit is used to determine the portion of the signal associated with the blood. This technique has two advantages. First, it results in a faster response time because there is no need to wait for heart beats. Second, there is less signal loss due to synchronous signal extraction (the synchronous method removes some blood associated signal unnecessarily).

Figure 9:
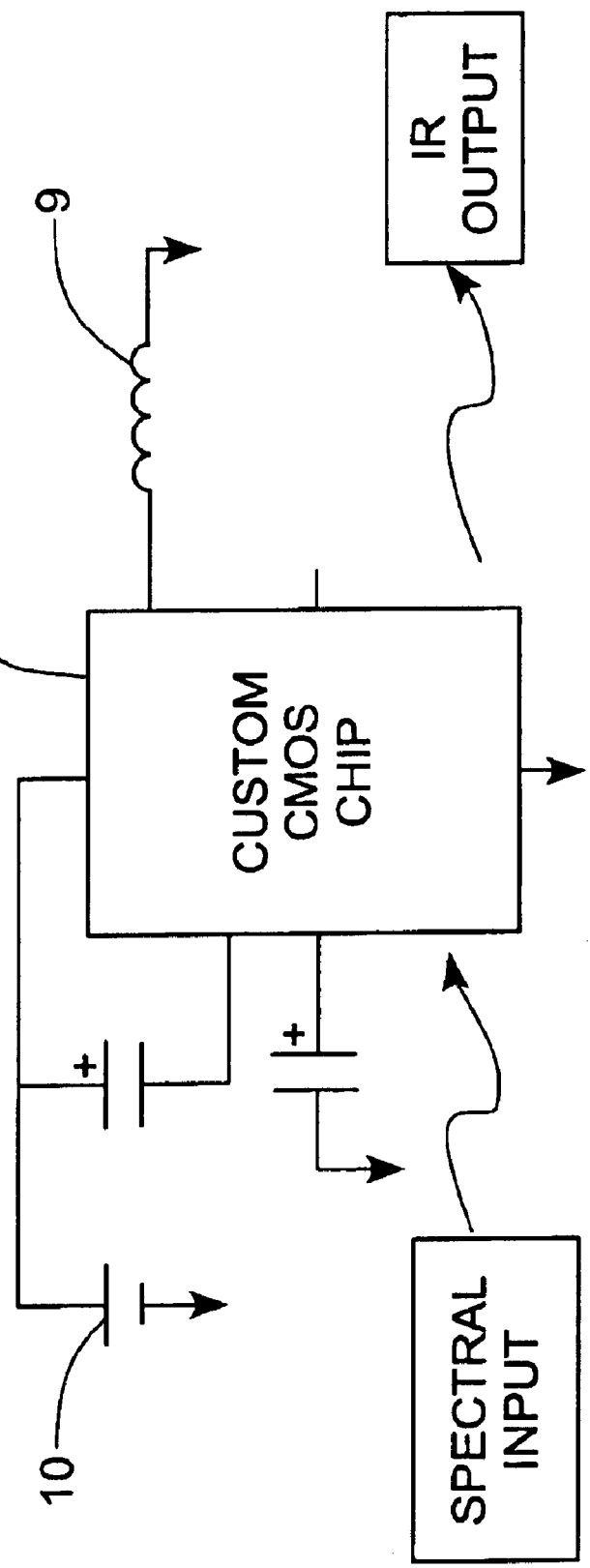
FIG. 9 is a block diagram of the preliminary schematic diagram for the sensor module.

FIG. 9 shows a preliminary schematic diagram for a sensor module. The sensor module is the portion of the analyte measuring device which is positioned on the target tissue and bears the radiation source and sensors, among other things. Everything is integrated onto a single CMOS chip 8 as shown, except the battery 10, radio antenna 9, and one or more capacitors (used, for example, as power filter and charge pump). FIG. 9 shows the sensor arrays integrated on the chip as well. Earlier, FIG. 3 depicted a separate light source mounted on the other side of the ear for measuring the transmission IR spectra transmitted. The schematic shown in FIG. 9 depicts the alternate embodiment, in which the light sources are also integrated onto the chip. While FIG. 3 shows transmission and FIG. 9 implies a reflection mode, both embodiments are fully encompassed by the present invention.

Figure 10:
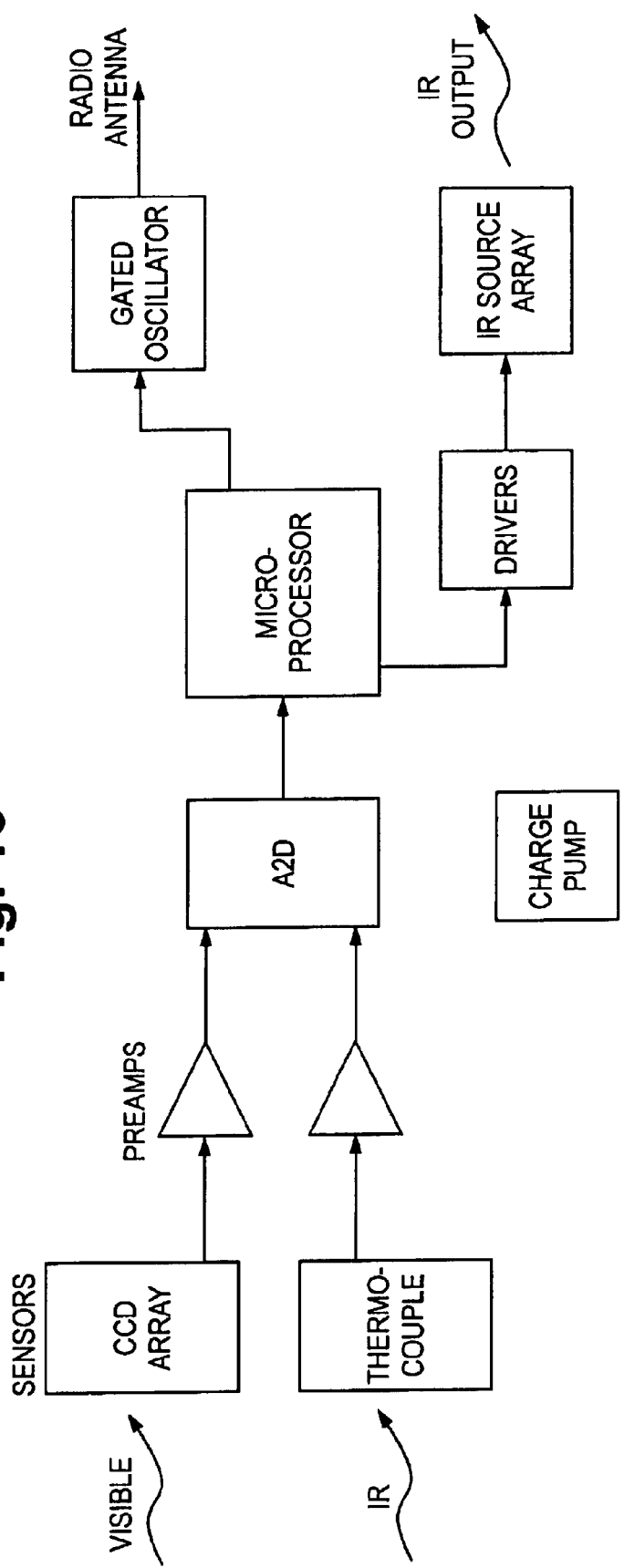
FIG. 10 is a block diagram of the CMOS custom chip for the sensor arrays.

FIG. 10 shows a block diagram of functions incorporated into the CMOS chip and the sensor arrays; one for visible light (e.g. a silicon CCD array), and one for the IR region (e.g. a thermocouple array). Preamplifiers are included for each sensor. The spectral data output from the sensors is digitized by the analog-to-digital converter. A charge pump to stabilize operating voltages and a gated RIP oscillator for the data transmitter are preferably included in the CMOS chip as well. One embodiment also includes integrated light sources. The block diagram shows a microprocessor embedded in the chip. However, a state table design is a viable alternative embodiment.

Figure 11:
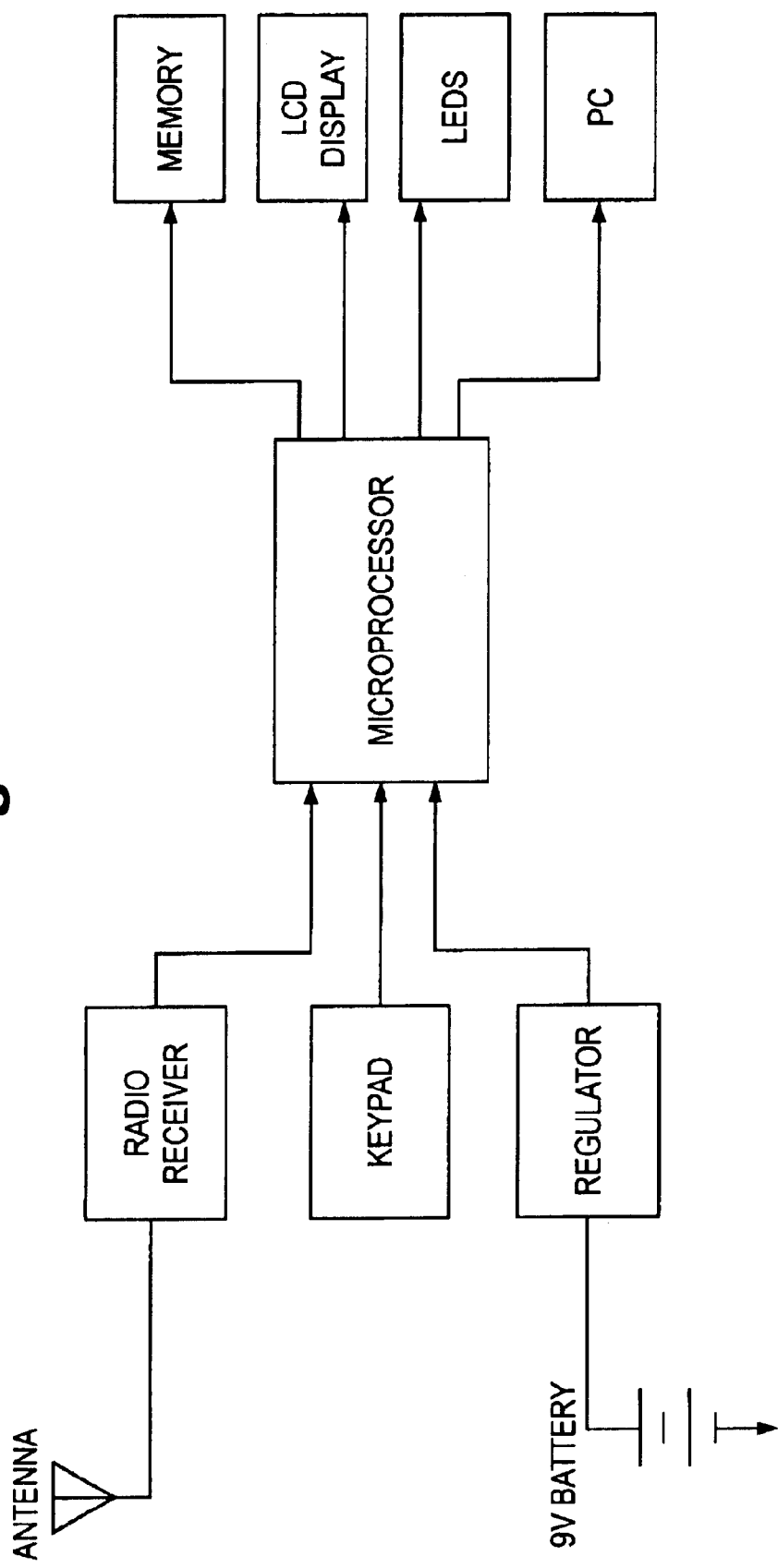
FIG. 11 is a block diagram of the inputs and outputs for the pocket monitor.

A "pocket monitor" is provided in a preferred embodiment for displaying analyte measurements in the field. A block diagram for the pocket monitor is shown in FIG. 11. For situations that require continuous monitoring, a pocket monitor may be dedicated to a specific individual for data logging and downloading (optional) to a computer at a more convenient time. The pocket monitor contains a radio receiver tuned to a specific sensor transmitter frequency. Data from the sensor module is received and processed for prompt display and storage. The pocket monitor also preferably utilizes an LCD display screen where data may be presented. A graphics mode showing analyte readings for the recent past can also be displayed.

Two preferred embodiments of the pocket monitor are described. The first utilizes existing IRDa hardware available in some personal computers. This embodiment eliminates the need for a separate receiver to be supplied by the personal computer. The second embodiment has a separate receiver that plugs into an existing I/O port in the personal computer. In this embodiment, the receiver accepts the low-power radio frequency transmissions either from the sensor module directly or from the pocket monitor, translates the transmission into an acceptable I/O format (e.g. RS-232), and then sends the information to the host personal computer via an I/O port. These two embodiments may alternately be combined for maximum flexibility.

The software package for the personal computer is based on a user-friendly platform (e.g. Windows 95). The software uses simple GUI (Graphic User Interface, e.g. Visual Basic) that allows for quick and easy results evaluation. The software takes the information received from the I/O port (e.g. an IRDa port or RS-232 port) and imports this information into a database. Algorithms evaluate the spectra data and provide the individual with readily understood information on concentrations of the analytes of interest. These results may be displayed on a "screen" on the personal computer monitor. Preferably, the software enables further analysis and manipulation of the analyte measurement data on the display. An alternative embodiment incorporates a modem feature that would allow a personal computer to transmit some or all of the information to a main computing center via information transmission means (e.g. a phone line). Data archiving would permit long term trending analysis of analyte concentration levels.

Spectrophotometry is an important aspect of the present invention. Currently many spectroscopic methods are in use covering all regions of the electromagnetic spectrum from x-ray to radio wavelengths. For the present invention, the x-ray and UV regions are not preferred because of the greater possibility of damage to the region of the body being tested. Although interesting, the radio region of the spectrum is also not preferred because the physical structures required to generate and sense radio signals differ substantially from those of the preferred embodiments. The preferred spectral regions for use by the analyte measuring device are thus the visible, near-infrared, and infrared regions of the spectrum.

Direct spectroscopic measurements of unmodified body fluids with the more traditional speactral regions (ultraviolet, visible and infrared) generally have limited penetration depths, and are hindered by interfering absorption and excessive scattering with inhomogeneous samples. Body fluids and soft tissues, in contrast, are relatively transparent at near-IR wavelengths. Thus, near-IR spectroscopy is preferred with the analyte measuring device of the present invention.

The spectral complexity of typical analytes helps isolate particular species out of the total spectra. For example, β-D-glucopyranose shows absorption peaks in the IR fingerprint region at 1458, 1435, 1365, 1325, 1235, 1205, 1152, 1109, 1080, 1035, and 996 $cm^{-1}$, and a mere listing of the peaks leaves out a great deal of the complexity of the actual spectra. Very high order polynomials (for example, with hundreds of terms) or tabular methods fitted to individual species spectra are used alongside multivariate analysis techniques or orthogonal function methods to capitalize on this inherent complexity. Effects of interfering compounds and overlapping peaks are part of the analysis and, due to the spectra complexity, tend to be compensated and even separated, if desired.

Because blood is a complex mixture, there are various ways of categorizing its many constituents. Table 1, for example, shows the basic separation of blood constituents into solids (formed elements) and liquids (blood plasma). The solids represent about 45% of the blood while liquids (55%) represents the rest. The components of interest for the present invention are contained in the plasma. As seen in Table 1, plasma is about 90% water, with another 8% as plasma proteins, leaving about 2% of the plasma for the analytes of interest. That is, 2% of 55% or roughly 1% of whole blood. Thus, the sensor module is configured to measure spectral amplitude significantly better than 1% (first estimate) in order to obtain data sufficiently accurate to resolve the analytes of interest.

substance is misleading because it does not differentiate between all of the spectroscopically distinct species of a given constituent. For example, glucose has three spectroscopically important species; the open ring, α-and β-pyranose forms. Similarly, hemoglobin has four distinct subunits. The present invention assumes that there are 102 important constituents, but the number is actually higher when considering the effect of various subspecies and subunits with distinct spectral characteristics. For blood analytes with concentrations comparable to or greater than glucose and lactate, Table 2 shows these blood components arranged in order of molar concentration. The components are arranged this way because the spectrum of each, as related by Beers' Law, is typically normalized against molar concentration. Supposing that the relative strength of the spectra correlates with molar concentration (not always true), the table provides an approximate ranking of the components that can be used to decide which ones must be retained for compensation when measuring an analyte (such as glucose). As seen in Table 2, glucose ranks $10^{th}$ and lactate ranks $16^{th}$. The other analyte ranking in Table 2 is by mass concentration. The larger molecules, such as hemoglobin or albumin, may have multiple absorbing sites per

TABLE 1

Blood Constituents

| Type | Constituent | | Characteristics/Functions |
|---|---|---|---|
| Formed Elements (45%) | Erythrocytes (98–99%) | | anucleate, contain hemoglobin; $O_2$ & $CO_2$ transport |
| | Leukocytes (0.1–0.3%) | Neutrophils (60–70%) | granulocytes, polymorphonuclear; phagocytosis, wound healing |
| | | Eosinophils (2–4%) | granulocytes, bilobed nucleus: phagocytosis |
| | | Basophils (0.5–1%) | granulocytes, 2–5 lobed nucleus; release histamine |
| | | Lymphocytes (20–25%) | agranulocytes, circular nucleus, T cells, B cells; immune response, antibodies |
| | | Monocytes (3–8%) | agranulocytes, large kidney-shaped nucleus; phagocytotic macrophages |
| | Thrombocytes (platelets) (1–2%) | | anucleate, megakaryocyte fragments; blood clotting |
| Blood Plasma (55%) | Water (90%) | | |
| | Plasma proteins (8%) | Albumin (54%) | maintain osmotic pressure between |
| | | Globulins (38%) | blood & tissue |
| | | Fibrinogen (7%) | |
| | | Others (1%) | lipid and metal ion transporters, antibodies clotting factor enzymes, hormones, clotting factors |
| | Electrolytes | $NA^+$, $K^+$, $Ca^{2+}$, $Mg^{2+}$, $Cl^-$, $HCO_3^-$, $SO_4^{2-}$, $HPO_4^{2-}$ | |
| | Gases | $O_2$, $CO_2$, $N_2$ | |
| | Nutrients | Glucose, other carbohydrates | sources of energy |
| | | Amino acids | protein building blocks |
| | | Lipids | fats, steroids, phospholipids |
| | | Cholesterol | component of plasma Membranes & steroid hormones |
| | Waste Products | Urea | From breakdown of proteins |
| | | Creatinine | from breakdown of creatine phosphate (from muscles) |
| | | Uric acid | from breakdown of nucleic acids |
| | | Bilirubin | from breakdown of hemoglobin |
| | Hormones | Various | |

There blood is a complex mixture; only 102 dominant constituents are present with concentrations varying from hemoglobin at about 15 g/dL to constituents such as insulin in the nanogram range and lower. However, this listing by molecule. Such multiple absorbing sites distort the molar ranking premise of only one or a small number of absorbing sites. Thus, the top ranked analytes, as ranked by mass concentration, are important as well.

For an individual analyte, Beers' Law takes the form A=εCb, where A is absorbance, ε, is the molecular extinction coefficient, C is the molar concentration, and b is the optical path length. The absorbance, A, is the logarithm of the transmittance. Preferably, the molar extinction coefficient, ε, is a function of wavelength, λ, alone. The molar extinction coefficient ε is measured over a range of wavelengths to form the absorption spectrum that would be associated with the particular analyte. The molar extinction coefficient, ε, is measured for each analyte of interest to form a set of spectra, ($\epsilon_1, \epsilon_2, \ldots, \epsilon_N$) over the wavelength range of interest. When more than one analyte is present, Beers' Law allows simple addition of the absorbance of each one.

$$A_{total}=A_1+A_2+ \ldots +A_N=C_1b\epsilon_1+C_2b\epsilon_2+ \ldots +C_Nb\epsilon_N$$

Presuming that the optical path length, b, is the same for all the analytes, this relation becomes:

$$A_{total}/b=C_1\epsilon_1+C_2\epsilon_2+ \ldots +C_N\epsilon_N$$

TABLE 2

Proposed Blood Analytes to Compensate.

| | Minimum | Maximum | |
|---|---|---|---|
| a). Dominant according to mass concentration in the blood. | | | |
| 1. Hemoglobin | 12000 | 18000 | mg/dL |
| 2. Albumin | 3200 | 5600 | mg/dL |
| 3. Globulins Total | 2300 | 3500 | mg/dL |
| 4. Complement Proteins, Total | 373 | 467 | mg/dL |
| 5. Fribrinogen | 200 | 400 | mg/dL |
| 6. Phospholipids | 150 | 380 | mg/dL |
| 7. Cholesterol | 150 | 250 | mg/dL |
| 8. Triodothyronine | 80 | 200 | mg/dL |
| 9. Triglyceriedes | 10 | 190 | mg/dL |
| 10. Glucose | 60 | 100 | mg/dL |
| 11. Non-protein Nitrogen | 25 | 50 | mg/dL |
| 12. Ceruloplasmin | 23 | 50 | mg/dL |
| 13. Protoporphyrin | 15 | 50 | mg/dL |
| 14. Glutathione | 24 | 37 | mg/dL |
| 15. Prealbumin | 15 | 36 | mg/dL |
| 16. Salicylates | 15 | 30 | mg/dL |
| 17. Urea Nitrogen | 8 | 23 | mg/dL |
| 18. Lactate (Lactic Acid) | 5 | 20 | mg/dL |
| b. Dominant analytes according to molar concentration in the blood. | | | |
| 1. Base, Total | 145 | 160 | mmol/L |
| 2. Sodium | 136 | 142 | mmol/L |
| 3. Chloride | 95 | 103 | mmol/L |
| 4. Non-protein Nitrogen | 18 | 36 | mmol/L |
| 5. Carbon Dioxide | 19 | 30 | mmol/L |
| 6. Bicarbonate | 21 | 28 | mmol/L |
| 7. Lipids, Fatty Acids | 9 | 15 | mmol/L |
| 8. Urea Nitrogen | 2.9 | 8.2 | mmol/L |
| 9. Cholesterol | 3.9 | 6.5 | mmol/L |
| 10. Glucose | 3.3 | 5.6 | mmol/L |
| 11. Potassium | 3.8 | 5 | mmol/L |
| 12. Alpha Amino Acid Nitrogen | 2.6 | 5 | mmol/L |
| 13. Lipids, Phospholipid Phosphorus | 2.6 | 3.6 | mmol/L |
| 14. Calcium | 2.3 | 2.7 | mmol/L |
| 15. Hemoglobin | 1.9 | 2.5 | mmol/L |
| 16. Lactate (Lactic Acid) | 0.3 | 2.2 | mmol/L |

The total absorbance divided by path length is seen to be a linear superposition of spectra, $\epsilon_i$, according to the molar concentration of each one, $C_i$. Note that the definition can be shifted to use mass concentration rather than molar concentration, even term-by-term, and Beers' law will still apply. In the application of Beers' Law to an unknown mixture, the set of spectra ($\epsilon_1, \epsilon_2, \ldots, \epsilon_N$) is assumed to be known by prior laboratory measurement. The optical path length, b, is also assumed to be known. (In the lab, $b_{lab}$ can be fixed precisely. But in the embodiment where analytes in the ear lobe are being measured and focusing is used, $b_{ear}$ may be a function of λ also.

Rewriting the absorbance relation one more time for composite spectrum (CS):

$$CS=A_{total}/b=C_1\epsilon_1+C_2\epsilon_2+ \ldots +C_N\epsilon_N$$

In the method of the present invention, the composite spectrum and reference spectra are measured. Thus, the concentration coefficients are determined using Beers' law.

Table 2 lists about 28 primary blood components. A molar extinction coefficient can be determined for each component so that all 28 terms are included. Of course, analytes beyond those listed in Table 2 may also be measured using the present invention. Determination of all 28 molar extenction coefficients, ε, is preferred. Alternately, the calculation may be limited to only the components that are prominent with respect to the analyte of interest. For example, glucose ranks $10^{th}$ in Table 2 molar concentration. Limiting the calculation to the analytes with 20% or more prominence with respect to glucose will give a model with sufficient accuracy for glucose determination, using perhaps only 25 or 30 terms.

Near IR spectroscopy has been used to extract the concentration of blood analytes such as albumin, glucose, triglycerides and others. Using this method, linear indications of the analyte concentration can be obtained, provided that everything is held constant except the analyte being measured. Usually a "baseline" or reference level must be established through other means. Attempts to measure glucose concentration using near IR spectroscopy have encountered difficulty, primarily from "baseline drift". As other analytes in the blood vary—for example, albumin—the measurement of glucose changes also. The glucose "baseline" shifts because of the albumin change, for example, causing erroneous glucose readings. In fact, a least squares fit of the albumin spectra, using the glucose spectra, yields a non-zero result which adds to the glucose component, hence a variable baseline. Other unknown components such as drugs can also cause shifts in the spectra.

The present invention preferably uses self calibration to compensate for the various problems encountered in the near-IR determination of blood analyte concentration. Self calibration relies on the ratio of analyte measurement against a reference material. For analyte measurement in blood, there are two reference materials present in all animals, namely hemoglobin and water. Measuring the concentrations of hemoglobin and water simultaneously with the analyte of interest, an arithmetic ratio may be calculated. This provides a number of advantages. First, the ratio conforms better to commonly accepted definition of concentration, i.e., the amount of analyte per unit of blood. Hemoglobin and water account for about 94% of blood, providing a good basis for the assessing of the amount of blood in the test volume. Second, measurement of hemoglobin and water at the same time as the analyte of interest means that variations that affect the analyte measurement also affects hemoglobin and water. Thus, the ratio should automatically compensate a substantial part of these variations. Third, since hemoglobin occurs only in the blood, it can be used to make a hematocrit determination, based on the proportion of blood by volume made up of erythrocytes, to separate blood and tissue.

If the pulsatile method is used to determine a signal associated with the arterial blood movement using the hemoglobin signal, then a ratio of pulsatile hemoglobin to total hemoglobin can be made. Call this ratio the P/B ratio. If the pulsatile component of the analyte of interest is found, the same moving volume is assumed and the P/B ratio used to determine how much of the analyte is in the blood, and how much is in the tissue. For a given analyte, once its fractions are known, the largest signal (usually the tissue signal) can be used to imply blood concentration because the fraction in the blood is not be expected to change very rapidly. The smaller pulsatile signal may then be re-measured over a longer time period, to improve accuracy, with the analyte fraction updated periodically. This method improves accuracy while allowing faster measurements and maintaining self calibration.

The method and apparatus of the present invention compensates for individual variation in measurement due to skin and tissue characteristics. Since the spectra of water and hemoglobin are well known, the spectrum of the skin and tissue may be determined simultaneously with the measurement of other analytes. A reference color is chosen corresponding to a prominent absorption peak (e.g., of water). For example, if water is the dominant absorber at a particular wavelength, then the rest of the spectrum may be corrected based on the known spectrum of water, at least over the wavelengths down to perhaps 700 nm where water becomes transparent. Similarly, the spectra may be corrected using other dominant absorbers at a particular wavelength. To continue with the water example, below a wavelength of 700 nm hemoglobin becomes the dominant absorber and can be used to extend the correction based on the known spectrum for hemoglobin down to near 450 nm. Correcting factors are thereby used to extract the dominant features of the skin and tissue. As additional analytes are extracted from the skin and tissue spectrum, a large spectrum remains that is associated only with the skin that exhibits a roughly constant absorbance of about 2. This spectral pattern is associated with chemical components not present in the blood. If the original reference wavelength were to produce an appreciable absorbance error, this would show up as a constant error over wavelength. Computing the ratio for the analyte of interest would cause this type of error to disappear since the analyte is affected the same way. The calculation may be corroborated by performing a similar calculation on the pulsatile spectra.

Overlapping peaks have previously made computing the concentration of a particular analyte using IR spectroscopy difficult, as it hard to distinguish between the portion of the peak caused by the analyte and that caused by other components present. One technique used to combat this problem is to compute the second derivative of the spectra to sharpen the peaks. This reduces the problem by reducing the amount of overlap, but does not solve it completely, because of the very large ratio between the concentration of interfering analytes and the analytes of interest. This effect is typically the major source of error in attempting to extract a single analyte such as glucose, or any analyte for that matter. The apparatus and method of the present invention preferably uses Linear Regression techniques (including partial least squares methods) and Orthogonal functions to correct for the problem of overlapping peaks and other spectral defects.

The present invention preferably utilizes linear regression or least squares technique. These methods produce an accurate measurement of analytes provided all the interaction terms are included. Hall and Pollard, referenced earlier, includes an excellent discussion of least squares fitting of data and the method of partial least squares for including interactions. The disclosure of this reference is hereby incorporated. These methods are useful in their own right, and may be used to determine the weighting function, w, described below.

A preferred embodiment of the present invention utilizes orthogonal function techniques. Orthogonal functions behave very much like vectors, and an "inner product" may be defined, $<\epsilon_1|w|\epsilon_2>$, where:

$$<\epsilon_1|w|\epsilon_2> = \int w\epsilon_1\epsilon_2 d\lambda$$

w=the weighting function (in $\lambda$)
$\epsilon_1$ and $\epsilon_2$ are functions defined over $\lambda$
$\lambda$ is the common parameter (wavelength)

The two functions $\epsilon_1$, and $\epsilon_2$ are said to be orthogonal if $<\epsilon_1|w|\epsilon_2> = 0$ for the weighting function w. Thus, the weighting function, w, acts to make the basis functions, or analyte spectra, orthogonal over the wavelength, $\lambda$, of interest. The weighting function is positive. Thus, adjustable candidate weighting functions include quadratics. Further, for functions to be orthogonal to one another, at least one of the basis functions must change sign over the interval in order for the defining integral to be zero. The basis functions, or analyte spectra in the present invention, are based upon absorption, which is always a positive number. In order to have a sign change, the first or second derivatives of the basis functions, or analyte spectra, may be taken. Alternately, the "ac" component (wherein the average value is subtracted) of the basis function, or analyte spectra, may be used.

To make two functions orthogonal, a single adjustable parameter is needed to find a weighting function. As an example, the water spectrum (which absorbs primarily at long wavelengths) can be made orthogonal to the deoxyhemoglobin spectrum (which absorbs primarily in the 500–600 nm region) if the "ac" method is used and the weighting function $(x-a)^2$ is used. The parameter, a, is adjusted until the defining integral is zero. Further, the four hemoglobin sub-types have sufficient features that they may also be made mutually orthogonal. For 28 basis functions, or analyte spectra, 378 (or 28×27/2) adjustable parameters are necessary to find a weighting function. Other methods for finding weighting functions may also be used. For example, one weighting function can be found that makes water orthogonal to the other 27 basis functions, which then requires only 27 adjustable parameters. This weighting function may then be used to decompose the water portion of the spectrum. Another weighting function may be found which makes Hb orthogonal to the remaining 26 basis functions (water already being removed). This second weighting function requires only 26 adjustable parameters. And so on for the remaining basis functions. The result is a set of 26 weighting functions rather than just one which accomplishes the same decomposition. Further, because the concentrations of the analytes drop off quickly, another possibility is to remove the analytes in groups. For example, water and the four kinds of hemoglobin may be removed first and the residual spectrum examined thereafter for another group of analytes.

There are many sets of orthogonal functions in common use which are defined along these lines. They include Legendre polynomials, Laguerre polynomials, Hermite polynomials, Chebychev polynomials and Ultraspherical polynomials, for example. Sin(n x) and cos(n x) form orthogonal sets also. Each of these sets has the orthogonality property $<\epsilon_N|w|\epsilon_M> = 0$ if $N \neq M$. The weighting function depends on the set used.

Generally, these sets of orthogonal functions ($\epsilon_1, \epsilon_2 \ldots, \epsilon_N$) are used to decompose a more complicated function CS into "components".

$$CS = C_1\epsilon_1 + C_2\epsilon_2 + \ldots + C_N\epsilon_N + \ldots$$

The value of any specific coefficient of interest, for example, the molar concentration of the nth component, $C_N$, is determined by using the orthogonality property. The composite spectrum, CS, is multiplied by the weighting function w and by the basis function, in the present invention the analyte spectra, associated with the coefficient of interest, for example, the molar extinction coefficient of the nth component, $\epsilon_N$. The result is integrated over $\lambda$, in the present invention, the wavelength of interest. All the terms on the right side of the equation are zero by orthogonality, except the one of interest, the molar extinction coefficient of the nth component, $\epsilon_N$.

$$\int w C S \epsilon_N d\lambda = C_N \int w \epsilon_N \epsilon_N d\lambda$$

And, $$C_N = \frac{\int w C S \epsilon_N d\lambda}{\int w C S \epsilon_N d\lambda} = \frac{\langle CS|w|\epsilon_N \rangle}{\langle \epsilon_N|w|\epsilon_N \rangle}$$

All of the coefficients may be determined this fashion.

IR and near-IR spectra may be analyzed using orthogonal functions as described above. The spectra for the blood analytes are used as basis functions and made orthogonal by proper selection of weighting function w. As explained above, the weighting function or functions are found that make the basis functions orthogonal over the wavelength range of interest. Note that the bulk of the calculations involving reference spectra and weighting functions are performed in the laboratory. The processor of the analyte measuring device can then calculate the result in as little time as a few seconds. The calculations necessary "in the field" consist of only one integration of the spectrum for each analyte. If 28 analytes are being considered, for example, and the integrations take only a millisecond or so (which is within the capacity of available processors), the 28 integrations necessary may be accomplished in under one second.

Because of the complexity of the individual spectra, high order polynomials are needed to fit them. The method and apparatus of the present invention can account for perhaps 100 analytes or more. The number of coefficients needed to determine the weighting function may then be on the order of several thousand. Thus the invention makes use of a matrix that is 1000×1000 or larger that must be inverted to determine the weighting function. This may be readily accomplished, as SPICE circuit simulations, for example, routinely invert matrices this size and larger, especially for transient simulations where the typical simulation inverts large matrices thousands of times in a typical run. Polynomial fitting of the spectra for glucose and albumin has also been accomplished using the Microsoft EXCEL matrix inverter. Microsoft EXCEL has built in functions to invert matrices up to 256×256 elements, which allows up to 256 data points to fit the spectra.

The use of orthogonal polynomials in this invention provides a distinct advantage over the use of linear regression. Using orthogonal polynomials, once the weighting function is known, $<\epsilon_N|w|\epsilon_N>$ is determined at the lab or factory, and only one integration, $<CS|w|\epsilon_N>$, is performed at the site "in the field" to determine the concentration of a specific analyte, such as glucose. In contrast, linear regression requires an iterative solution of multiple analytes simultaneously to extract the one of interest. It should be noted that the orthogonal function method also yields a weighted least squares fit of the data. Any of the currently used techniques, such as second derivative peak sharpening, may also be used to improve performance of the invention. Compensating for the 20 or 30 dominant background components eliminates the accuracy and baseline drift issues existing in previous efforts in this area.

The data processing of the present invention resolves numerous other problems as well. For example, overlapping peaks are corrected for by using orthogonal functions. Sample density variations are dealt with by measuring the sample average concentration. Over-fitting of the data may be a statistical problem and should be avoided in determining which $\epsilon$s should be used.

Computational problems may also have a negative impact on accuracy. A significant example of this is large concentration differences. For example, comparing albumin at 5 g/dL and glucose at 100 mg/dL represents a 50:1 concentration ratio. This has implications on the measurement accuracy required. Glucose absorbs at wavelengths where albumin does not, for example, so that the problem in this particular case is abated somewhat. The net numerical effect may be that albumin, measured at its absorption peaks, is used to compensate for albumin effects at the glucose peaks. Since $\epsilon$ for albumin is known, the method of orthogonal functions provides a strong advantage because it inherently compensates for the albumin effects at the glucose peak. Obtaining 10% glucose accuracy requires spectral absorbance measurements of 1% or better because of the concentration differences, but as mentioned earlier this is within the capability of the method and apparatus of the present invention.

While the embodiments and applications of this invention have been shown and described in detail, it will be apparent to those skilled in the art that many more modifications than mentioned above are possible without departing from the inventive concepts described herein. The scope of the present invention is thus limited only by the terms of the appended claims.

What is claimed is:

1. A method of non-invasively measuring the concentration of one or more blood analytes in a portion of tissue of a human or animal comprising the steps of:

positioning the portion of tissue near a light source and one or more sensors such that infrared radiation transmitted by the light source is reflected from or transmitted through the portion of tissue and onto the one or more sensors;

exposing the portion of tissue to infrared radiation from the light source;

detecting the infrared radiation transmitted or reflected from the portion of tissue with the one or more sensors;

generating spectral data from the one or more sensors in response to receiving the infrared radiation and communicating the spectral data to a processor;

determining the concentration of one or more blood analytes by orthogonal analysis using self calibration of the spectral data in which the ratio of blood analyte to a blood reference material is used; and displaying the concentration of the one or more blood analytes.

2. The method of claim 1, wherein step of determining the concentration of one or more blood analytes by orthogonal analysis further includes using weighting functions.

3. The method of claim 2, further including the step of filtering the radiation from the tissue into a plurality of wavelengths before it is detected by the one or more sensors.

4. The method of claim 2, wherein the portion of tissue is an earlobe.

5. The method of claim 2, wherein the blood analyte is lactic acid.

6. The method of claim 2, wherein the blood reference material is selected from the group consisting of water and hemoglobin.

7. The method of claim 2, further including the step of separating the one or more blood analytes by using a ratio of pulsatile hemoglobin to total hemoglobin.

8. The method of claim 2 wherein the concentration of the one or more blood analytes is determined in less than 5 seconds.

9. The method of claim 2, wherein the steps of:
exposing the tissue to infrared radiation,
detecting the infrared radiation,
generating spectral data and communicating it to a processor,
determining the concentration of one or more blood analytes by orthogonal analysis using weighting functions and self calibration of the spectral data in which the ratio of blood analyte to a blood reference material is used; and
displaying the concentration of the one or more blood analytes,
are rapidly repeated to provide continuous information on blood analyte concentrations.

10. The method of claim 9, wherein the human or animal remains ambulatory during the measurement of blood analyte concentrations.

11. A method of detecting injury or fatigue in humans or animals including the steps of:
positioning a portion of tissue near a light source and one or more sensors such that infrared radiation transmitted by the light source is reflected from or transmitted through the portion of tissue and onto the one or more sensors;
exposing the portion of tissue to infrared radiation from the light source;
detecting the infrared radiation transmitted or reflected from the portion of tissue with the one or more sensors;
generating spectral data from the one or more sensors in response to receiving the infrared radiation and communicating the spectral data to a processor;
determining the concentration of lactic acid by orthogonal analysis using weighting functions and self calibration of the spectral data in which the ratio of lactic acid to a blood reference material is used; and
displaying the concentration of the lactic acid.

12. The method of claim 11, wherein the steps of:
exposing the tissue to infrared radiation,
detecting the infrared radiation,
generating spectral data and communicating it to a processor,
determining the concentration of lactic acid by orthogonal analysis using weighting functions and self calibration of the spectral data in which the ratio of lactic acid to a blood reference material is used; and
displaying the concentration of lactic acid,
are rapidly repeated to provide continuous information on lactic acid concentration.

13. The method of claim 12, further including the step of issuing a warning signal when lactic acid levels rise above a predetermined level.

14. A mobile apparatus for the non-invasive measurement of the concentration of one or more blood analytes in the blood of a portion of tissue comprising:
a light source for generating a spectrum of infrared radiation and transmitting the spectrum of radiation to the portion of tissue;
one or more sensors for detecting radiation from the portion of tissue over a broad spectrum and generating an output regarding the detected radiation;
a mounting device for positioning the light source and the one or more sensors approximately adjacent to the portion of tissue;
a processor for receiving the output from the sensors, the processor being configured for performing orthogonal analysis using weighting functions to determine the concentration of one or more blood analytes in the blood of the portion of tissue using self calibration in which the ratio of blood analyte to a blood reference material is used; and
a display for displaying the concentration of the one or more blood analytes.

15. The mobile apparatus of claim 14, wherein the one or more sensors are configured for detecting infrared radiation reflected from the portion of tissue.

16. The mobile apparatus of claim 14, wherein the one or more sensors are configured for detecting infrared radiation transmitted through the portion of tissue.

17. The mobile apparatus of claim 14, further including a source optics device for focusing the infrared radiation from the light source onto a measurement point on the portion of tissue.

18. The mobile apparatus of claim 17, further including a collimator for focusing infrared radiation onto the one or more sensors after it has passed through or reflected from the portion of tissue.

19. The mobile apparatus of claim 18, wherein the mobile apparatus comprises a pocket monitor module and a sensor module capable of communication with the pocket monitor module.

20. The mobile apparatus of claim 19, wherein the sensor module comprises the light source, the one or more sensors, the source optics device, the collimator, and the mounting device.

21. The mobile apparatus of claim 19, wherein the sensor module comprises two microprocessor chips and wherein the light source is mounted to one microprocessor chip and the one or more sensors are mounted on the other microprocessor chip.

22. The mobile apparatus of claim 20, wherein the sensor module comprises a radio frequency transmitter and the pocket monitor module comprises a radio frequency receiver.

23. The mobile apparatus of claim 22, wherein the sensor module further comprises the mounting apparatus for positioning the light source and the one or more sensors approximately adjacent to the portion of tissue, and wherein the portion of tissue comprises an ear lobe.

24. The mobile apparatus of claim 14, wherein the one or more sensors are capable of detecting near infrared regions of wavelengths of about 700 nm to about 2500 nm.

25. The mobile apparatus of claim 14, wherein the mobile apparatus is adapted to detect blood analytes with an error margin of 10% or less.

26. The mobile apparatus of claim 14, wherein the sensors comprise direct silicon sensors sensitive to radiation of a wavelength range from about 0.4 to 1.1 microns and infrared sensors sensitive to radiation of a wavelength range from 1 to 10 microns.

27. The mobile apparatus of claim 26, wherein the infrared sensors are thermocouples comprising two metal layers and a gold black layer.

28. The mobile apparatus of claim 27, wherein one of the two metal layers comprises a nickel-chromium alloy while the other of the two metal layers comprises a nickel-copper alloy.

29. The mobile apparatus of claim 14, further including a filter for separating radiation from the portion of tissue into various wavelengths, the filter being positioned such that the infrared radiation from the tissue passes through the filter prior to detection by the one or more sensors.

30. An ambulatory system for the rapid and continuous, non-invasive measurement of the concentration of one or more blood analytes comprising a sensor module and a pocket monitor module, wherein the sensor module comprises:

a light source for generating and transmitting infrared radiation to an ear lobe;

a focusing device for focusing the infrared radiation from the light source onto a measurement point on the ear lobe;

a filter for separating the infrared radiation into separate wavelengths;

one or more sensors for detecting infrared radiation transmitted or reflected from the measurement point and generating spectral data corresponding to the detected infrared radiation received;

a means for mounting the light source, the focusing device, the filter, and the one or more sensors on the ear lobe to facilitate the transmission of infrared radiation through the earlobe and to the one or more sensors;

a processor for receiving spectral data from the sensors, the processor being configured for performing orthogonal analysis to determine blood analyte concentration data using self calibration in which the ratio of one or more blood analytes to a blood reference material is used; and a radio frequency transmitter for transmitting the blood analyte concentration data over a short distance; and the pocket monitor module comprises:

a radio frequency receiver for obtaining blood analyte concentration data from the sensor module; and a monitor for displaying the blood analyte concentration data.

31. The ambulatory system of claim 30, wherein the sensor module further includes a collimator for refocusing the infrared radiation after scattering in the ear lobe.

* * * * *